United States Patent [19]
Hickle et al.

[11] Patent Number: 5,888,503
[45] Date of Patent: Mar. 30, 1999

[54] MATERIALS AND METHODS FOR THE CONTROL OF CALLIPHORIDAE PESTS

[75] Inventors: Leslie A. Hickle; Jewel Payne, both of San Diego, Calif.

[73] Assignee: Mycogen Corporation, San Diego, Calif.

[21] Appl. No.: 856,226

[22] Filed: May 14, 1997

Related U.S. Application Data

[62] Division of Ser. No. 249,780, May 26, 1994, abandoned, which is a division of Ser. No. 93,199, Jul. 15, 1993, abandoned.

[51] Int. Cl.$^6$ .......................... A01N 63/00; A01N 63/02
[52] U.S. Cl. ...................... 424/93.461; 424/93.2; 424/405; 424/409; 424/410; 435/69.1; 435/252.5; 435/254.11; 435/325; 514/2; 530/350; 536/23.71
[58] Field of Search ................ 424/93.2, 93.461, 424/405, 409, 410; 514/2; 530/350; 435/252.5, 254.11, 325, 69.1; 536/23.71

[56] References Cited

U.S. PATENT DOCUMENTS

| | | |
|---|---|---|
| 4,448,885 | 5/1984 | Schnepf et al. . |
| 4,467,036 | 8/1984 | Schnepf et al. . |
| 4,797,276 | 1/1989 | Herrnstadt et al. . |
| 4,849,217 | 7/1989 | Soares et al. . |
| 4,853,331 | 8/1989 | Herrnstadt et al. . |
| 4,948,734 | 8/1990 | Edwards et al. . |
| 4,999,192 | 3/1991 | Payne et al. ........................ 424/93 |
| 5,143,905 | 9/1992 | Sivasubramanian et al. .......... 514/21 |
| 5,151,363 | 9/1992 | Payne . |
| 5,229,292 | 7/1993 | Stock et al. ..................... 435/252.34 |

FOREIGN PATENT DOCUMENTS

| | | |
|---|---|---|
| 565082 | 11/1984 | Australia . |
| 0457498 | of 0000 | European Pat. Off. . |
| 0409438 | 1/1991 | European Pat. Off. . |
| 0480762 | 4/1992 | European Pat. Off. . |

OTHER PUBLICATIONS

Lyness et al. Microbial ecology of sheep fleece. Agricultural Ecosystems & Environment. vol. 49, No. 1, pp. 103–112, May 1994.

Padua et al. Development of microbial pesticide for mosquito control in the Philippines. Isreal Journal of Entomology. vol. 23, pp. 59–62, 1989.

Gaertner, F., L. Kim (1988) "Current Applied Recombinant DNA Projects" TIBTECH 6(4):S4–S7.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

Gaertner, F. (1989) "Cellular delivery systems for insecticidal proteins: living and non–living microoganisms" Controlled Delivery of Crop–Protection Agents, pp. 245–255.

Krieg, V.A. et al. (1983) "*Bacillus thuringiensis* var. *tenebrionis*: ein neuer, gegenuber Larven von Coleopteran wirksamer Pathotyp" Z. ang. Ent. 96:500–508.

Hofte, H., H.R. Whiteley (1989) "Insecticidal Crystal Proteins of *Bacillus thuringiensis*" Microbiological Reviews 53(2):242–255.

Feitelson, J.S., J. Payne, L. Kim (1992) "*Bacillus thuringiensis*: Insects and Beyond" Bio/Technology 10:271–275.

Schnepf, H.E., H.R. Whiteley (1981) "Cloning and expression of the *Bacillus thuringiensis* crystal protein gene in *Escherichia coli* " Proc. Natl. Acad. Sci. USA 78(5):2893–2897.

Aronson, A.I. et al. (1986) "*Bacillus thuringiensis* and Related Insect Pathogens" Microbiological Reviews 50(1):1–24.

Pinnock, D.E. (1994) "The use of *Bacillus thuringiensis* for control of pests of livestock" Agriculture, Ecosystems and Environment 49:59–63.

*Primary Examiner*—Elizabeth Kemmerer
*Assistant Examiner*—David S. Romeo
*Attorney, Agent, or Firm*—Saliwanchik, Lloyd & Saliwanchik

[57] ABSTRACT

Methods and compositions for the control of pests of the family Calliphoridae are described. Specifically, *Bacillus thuringiensis* (*B.t.*) isolates having anti-calliphorid activity are disclosed. Also described are recombinant hosts which express *B.t.* genes coding for pesticidal toxins. The *B.t.* isolates and recombinant proteins are shown to be useful in a method for controlling calliphorids including screwworms and the sheep blowfly.

8 Claims, No Drawings

MATERIALS AND METHODS FOR THE CONTROL OF CALLIPHORIDAE PESTS

This is a divisional of application Ser. No. 08/249,780, filed May 26, 1994, now abandoned; which is a divisional of application Ser. No. 08/093,199, filed Jul. 15, 1993, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopicallyas distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxingenes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a delta endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *san diego* (a.k.a. *B.t. tenebrionis*, a.k.a. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera-and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whitely [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli*. U.S. Pat. Nos. 4,797,276 and 4,853,331 disclose *B. thuringiensis* strain *san diego* (a.k.a. *B.t. tenebrionis*, a.k.a. M-7) which can be used to control coleopteran pests in various environments. U.S. Pat. No. 4,849,217 discloses *B.t.* isolates which have activity against the alfalfa weevil. U.S. Pat. No. 5,151,363 and U.S. Pat. No. 4,948,734 disclose certain isolates of *B.t.* which have activity against nematodes. Certain *B.t.* isolates have been described that have activity against flies, Australian Patent Publication No. AU-565082. These isolates are not, however, those isolates disclosed and claimed herein. Many other patents have issued for new *B.t.* isolates and new uses of *B.t.* isolates. The discovery of new *B.t.* isolates and new uses of known *B.t.* isolates remains an empirical, unpredictable art.

The Calliphoridae family, together with the Sarcophagidae and the Oestridae families, contain the species responsible for the most important myiases of domestic animals and man. Myiasis is the infestation of living animals with the larvae of dipteran flies. Myiasis caused by members of the family Calliphoridae is commonly called "blowfly strike." The "blow" is the laying of the eggs by the fly at or near a strike site. The "strike" is the development of the eggs into maggots and the damage that this development causes at that site. Strikes are classified by the area of the body affected.

Blowfly myiasis primarily affects sheep; however, many other animals may be affected. Major species of blowflies include *Lucilia sericata* (greenbottles), *Phormia terraenovae* (blackbottles), *Calliphora erythrocephala* and *C. vomitoria* (bluebottles) in Europe. These flies are characterized by the color of the metallic sheen on their body sections. *Lucilia cuprina, L. caeser, L. illustris, Phormia regina, Calliphora stygia, C australis, C. fallax, Chrysomyia albiceps, C. chlorophyga, C. micropogon,* and *C. rufifacies* are major species of blowflies in the tropics and subtropics.

The blowflies that attack sheep fall into two main categories:

(1) Primary flies, which are capable of initiating a strike on living sheep. These include Lucilia and *Phormia spp.* and some *Calliphora spp.*

(2) Secondary flies, which cannot initiate a strike, but attack an area already struck or otherwise damaged. They frequently extend the injury, rendering the strike one of great severity. Examples include many *Calliphora spp.* and, in warmer climates, *Chrysomyia spp.*

Eggs laid on the wool of sheep by primary flies, under favorable conditions, hatch within 12 hours. The hatched larvae migrate down the wool to the skin where the larvae lacerate the skin with their oral hooks and secrete proteolytic enzymes into the skin to establish the lesion. The larvae feed on the surrounding tissues, grow rapidly, and moult twice before becoming fully mature maggots. The maggots then drop to the ground and develop into mature flies. During the period of larval development, extensive tissue damage occurs, and the strike becomes available for the establishment of secondary infections or, worse, becomes an attractive site in which secondary blowflies may lay their eggs.

The irritation and distress caused by blowfly strikes are extremely debilitating, and sheep can rapidly lose condition. Where death occurs, it is often due to septicaemia. Affected sheep are anorexic, appear dull, and usually stay away from the main flock. Current methods of control are based primarily on the prophylactic treatment of sheep with insecticides. The problems associated with this are the relatively short period spent by the larvae on the sheep, the repeated infestations that occur throughout the season, and the rapidity with which severe damage occurs. Any insecticide used must therefore not only kill the larvae, but persist in the fleece. In this respect, the chlorinated hydrocarbon, dieldrin, proved particularly effective and gave protection for at least 20 weeks. However, this product has been largely withdrawn on safety grounds and replaced mainly by organophosphorus compounds, which have a persistence of 10–16 weeks unless resistance supervenes wherein this period becomes much shorter.

Application of these insecticides is made by plunge dipping or, more rarely in Europe, in a spray race or by jetting. In Europe, the high prevalence of body strike makes whole body protection necessary, and therefore the use of dips is more effective. In practice, an annual dip, usually in June, should give protection for the remainder of the fly season, but a second dipping in August may be necessary in order to ensure complete protection.

The name screw-worm is given to the larvae of certain species of Cochliomyia (syn. Callitroga) including *C. hominivorax* and *C. macellaria*, and to that of a single species of Chrysomyia, *C. bezziani*, which cause screw-worm myiasis in animals and occasionally man. Cochliomyia is found in the New World, while *C. bezziani* is confined to Africa and Asia.

The bluish-green flies have longitudinal stripes on the thorax and orange-brown eyes (Pl. IX). They occur primarily in tropical areas and lay their eggs on wounds, the larval stages characteristicallyfeeding as a colony and penetrating the tissues creating a large and foul-smelling lesion. *C. hominivorox* was such a problem in the southern United States that a mass eradication campaign using biological control was undertaken. This involved the release of up to 1,000 male flies, sterilized by irradiation, per square mile. Since the female fly mates only once, control proved very successful except where the flies, which are capable of flying up to 200 miles, migrated from across the Mexican border.

Regular use of chemicals to control unwanted organisms can select for drug resistant strains. This has occurred in many species of economically important pests. Biological control programs circumvent the selection problem of drug resistance and are ecologically favored; however, as illustrated by the use in screw-worm control, can be limited by the biology of the fly. The development of drug resistance and the limitations of biological control programs necessitate a continuing search for new control agents having different modes of action.

At the present time there is a need to have more effective means to control these pests that cause considerable damage to susceptible hosts. Advantageously, such effective means would employ biological agents.

BRIEF SUMMARY OF THE INVENTION

The subject invention concerns novel materials and methods for controlling pests of the family Calliphoridae. The materials and methods of the subject invention result from the unexpected discovery that certain *B.t.* isolates have activity against these pests. Specifically exemplified herein is activity against screw-worms and the sheep blowfly.

More specifically, the methods of the subject invention use *B.t.* microbes, or variants thereof, and/or their toxins, to control Calliphoridae. Specific *B.t.* microbes useful according to the invention are *B.t.* PS123D1, *B.t.* PS71M3, *B.t.* PS63B, *B.t.* PS52A1, *B.t.* PS80JJ1, *B.t.* PS204G6, *B.t.* PS91C2, *B.t.* PS173A, *B.t.* PS31J2, *B.t.* PS201T6, *B.t.* PS86Q3, *B.t.* PS74G1, *B.t.* PS33F2, *B.t.* PS202U2, *B.t.* PS83E5, *B.t.* PS84C3, *B.t.* PS204C3, *B.t.* PS207B6, and *B.t.* PS211B2. Further, the subject invention includes the use of variants of the exemplified *B.t.* isolates which have substantially the same calliphorid-active properties as the specifically exemplified *B.t.* isolates. Such variants would include, for example, mutants. Procedures for making mutants are well known in the microbiological art. Ultraviolet light and nitrosoguanidine are used extensively toward this end.

The subject invention also includes the use of genes from the *B.t.* isolates of the invention which genes encode the calliphorid-active toxins.

Still further, the invention also includes the treatment of substantially intact *B.t.* cells, or recombinant cells containing the genes of the invention, to prolong the calliphorid activity when the substantially intact cells are applied to the environment of a target pest. Such treatment can be by chemical or physical means, or a combination of chemical and physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

BRIEF DESCRIPTION OF THE SEQUENCES

SEQ ID NO. 1 is the N-terminal amino acid sequence of 86Q3(a).

SEQ ID NO. 2 is the N-terminal amino acid sequence of 63B.

SEQ ID NO. 3 is the N-terminal amino acid sequence of 52A1.

SEQ ID NO. 4 is the N-terminal amino acid sequence of 33F2.

SEQ ID NO. 5 is an internal amino acid sequence for 63B(2).

SEQ ID NO. 6 is an oligonucleotideprimer used according to the subject invention.

SEQ ID NO. 7 is an oligonucleotide primer used according to the subject invention.

SEQ ID NO. 8 is the forward oligonucleotide primer for 63B-A.

SEQ ID NO. 9 is the reverse oligonucleotide primer for 63B-INT.

SEQ ID NO. 10 is the oligonucleotide probe 33F2A.

SEQ ID NO. 11 is the oligonucleotide probe 33F2B.

SEQ ID NO. 12 is a reverse primer according to the subject invention.

SEQ ID NO. 13 is an oligonucleotide 5Q primer derived from the N-terminal amino acid sequence of SEQ ID NO. 1 (86Q3(a)).

SEQ ID NO. 14 is the amino acid sequence encoded by the oligonucleotide of SEQ ID NO. 15.

SEQ ID NO. 15 is a 3Q reverse oligonucleotideprimer used according to the subject invention.

SEQ ID NO. 16 is the amino acid sequence encoded by the oligonucleotide of SEQ ID NO. 17.

SEQ ID NO. 17 is 3Q reverse oligonucleotide primer used according to the subject invention.

SEQ ID NO. 18 is the oligonucleotide probe 52A 1-C.

SEQ ID NO. 19 is a forward oligonucleotide primer used according to the subject invention.

SEQ ID NO. 20 is a reverse oligonucleotide primer used according to the subject invention.

SEQ ID NO. 21 is an oligonucleotideprobe used according to the subject invention.

SEQ ID NO. 22 is an oligonucleotide probe used according to the subject invention.

SEQ ID NO. 23 is the B.t. universal primer.

SEQ ID NO. 24 is a gene-specific primer used according to the subject invention.

SEQ ID NO. 25 is a promoter sequence-primer used according to the subject invention.

SEQ ID NO. 26 is an oligonucleotideprimer used according to the subject invention.

SEQ ID NO. 27 is the nucleotide sequence encoding an approximately 130 kD B.t. toxin.

SEQ ID NO. 28 is the deduced amino acid sequence of the approximately 130 kD B.t. toxin encoded by SEQ ID NO. 27.

SEQ ID NO. 29 is an oligonucleotide probe used according to the subject invention.

SEQ ID NO. 30 is the nucleotide sequence encoding an approximately 77 kD B.t. toxin.

SEQ ID NO. 31 is the deduced amino acid sequence of the approximately 77 kD B.t. toxin encoded by SEQ ID NO. 30.

DETAILED DISCLOSURE OF THE INVENTION

The subject invention concerns the use of selected strains of Bacillus thuringiensis for the control of calliphorid pests.

Specific Bacillus thuringiensis isolates useful according to the subject invention have the following characteristics in their biologically pure form:

TABLE 1

Characteristics of Bacillus thuringiensis strains with sheep blowfly activity

| B.t. strain | Inclusion type | Approx. mol wt. of protein | Serovar |
| --- | --- | --- | --- |
| PS123D1 | Amorphic | 133, 67, 27 | israelensis |
| PS71M3 | Amorphic | 142, 133, 67, 27 | morrisoni |
| PS63B | Amorphic | 84, 82, 78 | wuhanensis |
| PS52A1 | Multiple attached | 58, 45 | wuhanensis |
| PS80JJ1 | Multiple | 130, 90, 47, 37 | sotto |
| PS204G6 | Long amorphic | 23, 21 | wuhanensis |
| PS91C2 | Bipyramid | 130 | morrisoni |
| PS173A | Amorphic | 133, 67, 27 | israelensis |
| PS31J2 | Flat square & diamond | 64, 33 | morrisoni |
| PS201T6 | Bipyramid & elliptical | 133, 31 | neoleonensis |
| PS86Q3 | Long amorphic | 155, 135, 98, 58 | new serovar |
| PS74G1 | Amorphic | 140, 135, 112, 105, 63 | darmstadiensis |
| PS33F2 | Bipyramid | 140, 94 | wuhanensis |
| PS202U2 | Multiple attached | 58, 45 | wuhanensis |
| PS83E5 | Multiple | 42, 37 | wuhanensis |
| PS84C3 | Large amorphic | 70, 41, 36, 35 | entomocidus |
| PS204C3 | Multiple | 110, 105, 62, 45, 39 | wuhanensis |
| PS207B6 | Amorphic | 39, 29 | wuhanensis |
| PS211B2 | Large amorphic & ellipse | 83, 70, 41, 36, 35 | entomocidus |

B.t. isolates useful according to the subject invention have been deposited. Also deposited are recombinant microbes comprising the B.t. genes of interest.

TABLE 2

Deposit information for B.t. strains

| B.t. strain | Accession Number | Deposit date |
| --- | --- | --- |
| PS123D1 | NRRL B-21011 | October 13, 1992 |
| PS71M3 | NRRL B-18930 | December 27, 1991 |
| PS63B | NRRL B-48246 | July 28, 1987 |
| PS52A1 | NRRL B-18245 | July 28, 1987 |
| PS80JJ1 | NRRL B-18679 | July 17, 1990 |
| PS204G6 | NRRL B-18686 | July 17, 1990 |
| PS91C2 | NRRL B-18931 | December 27, 1991 |
| PS173A | NRRL B-21010 | October 13, 1992 |
| PS31J2 | NRRL B-21009 | October 13, 1992 |
| PS201T6 | NRRL B-18750 | January 9, 1991 |
| PS86Q3 | NRRL B-18765 | February 6, 1991 |
| PS74G1 | NRRL B-18397 | August 16, 1988 |
| PS33F2 | NRRL B-18244 | July 28, 1987 |
| PS202U2 | NRRL B-18832 | May 31, 1991 |
| PS83E5 | NRRL B-18782 | March 7, 1991 |
| PS84C3 | NRRL B-18399 | August 16, 1988 |
| PS204C3 | NRRL B-21008 | October 6, 1992 |
| PS207B6 | NRRL B-21007 | October 6, 1992 |
| PS211B2 | NRRL B-18921 | November 15, 1991 |
| E. coli NM522(pMYC2361) | NRRL B-21016N | December 17, 1992 |
| E. coli NM522(pMYC2357) | NRRL B-21017 | December 2, 1992 |
| E. coli NM522 (pMYC2362) | NRRL B-21018 | December 2, 1992 |

The cultures are on deposit in the permanent collection of the Northern Research Laboratory, U.S. Department of Agriculture, Peoria, Ill., USA.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

Genes and toxins. The genes and toxins useful according to the subject invention include not only the full length sequences disclosed herein but also fragments of these sequences, or fusion proteins, which retain the characteristic pesticidal activity of the toxins specifically exemplified herein.

It should be apparent to a person skilled in this art that genes coding for calliphoridactive toxins can be identified and obtained through several means. The specific genes exemplified herein may be obtained from the isolates deposited at a culture depository as described above. These genes, or portions or variants thereof, may also be constructed synthetically, for example, by use of a gene machine. As used herein, the terms "variants" or "variations" of genes refer to nucleotide sequences which code for the same toxins or which code for equivalent toxins having calliphorid activity. As used herein, the term "equivalent toxins" refers to toxins having the same or essentially the same biological activity against calliphorid pests as the claimed toxins. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematicallycut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct within other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample have substantial homology. The probe's detectable label provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures.

These fragments and mutations, which retain the pesticidal activity of the exemplified toxins, would be within the scope of the subject invention. Also, because of the redundancy of the genetic code, a variety of different DNA sequences can encode the amino acid sequence disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining calliphorid activity are also included in this definition. As used herein, the phrase "calliphorid activity" includes activity against calliphorid larvae as well as other stages of development.

Certain toxins of the subject invention have been specifically exemplified herein. Since these toxins are merely exemplary of the toxins of the subject invention, it should be readily apparent that the subject invention further comprises variant or equivalent toxins (and nucleotide sequences coding for variant toxins) having the same or essentially the same biological activity against calliphorids of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts. The toxin-encoding genes harbored by the isolates of the subject invention can be introduced into a wide variety of microbial, plant, or animal hosts. Expression of the toxin gene results, directly or indirectly, in the intracellularproduction and maintenance of the pesticide. With suitable microbial hosts, e.g., Pseudomonas, the microbes can be applied to the situs of calliphorids where they will proliferate and be ingested by the pest. The result is a control of this pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the pest environment. These microorganisms are selected so as to be capable of successfully competing in that environment with the wild-type microorganisms that are present. The microorganism host must also provide for stable maintenance and expression of the gene expressing the polypeptide pesticide, and, desirably, provide for improved protection of the pesticide from environmental degradation and inactivation.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularlyhalogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of cell treatment retains at least a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA constructprovides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. The *B.t.* cells may be formulated in a variety of ways. In a preferred embodiment the *B.t.* cells or the toxin is applied as a drench. In a further embodiment of the invention, *B.t.* cells or toxin are presented to the fly in a "bait bin." Formulations applicable for use with these embodiments include wettable powders, granules or dusts, and mixtures with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The *B.t.* toxins of the invention can be administered as a liquid drench when used against calliphorids on sheep or other animals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight.

Where it is desired to administer the toxin compounds in a dry form, these forms are prepared by intimately and uniformly mixing the active ingredient with suitable finely divided diluents, fillers, disintegrating agents and/or binders such as starch, lactose, talc, magnesium stearate, vegetable gums and the like. Such formulations may be varied widely with respect to their total weight and content of the antiparasitic agent, depending upon the factors such as the type of host animal to be treated, the severity and type of infection and the weight of the host.

The methods and compositions of the subject invention can be used to control calliphorids, which can parasitize vertebrates. Specifically, the invention can be used to control calliphorids in humans, livestock, domestic pets, and other animals. As used herein, the term "livestock" can include, for example, sheep, cattle, pigs, and goats. The methods and compositions of the subject invention may be used to control immature and adult calliphorids. The methods of control include, but are not limited to, direct application to the animal coat. The B.t. toxins described herein may be used alone, or in rotation or combination with other anti-calliphorid chemicals.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., wool, by spraying, dusting, sprinkling, or the like.

In a further embodiment of the invention, the B.t. cells or toxin are presented to the fly in a "bait bin." A bait bin comprises a large, covered bin containing an attractant, i.e., part of a carcass, to attract and "trap" the flies. The flies are exposed to the toxin after being "trapped" within the bin. A bait bin is most effective when placed in areas where sheep are handled, such as in shearing sheds or yards. A bait bin should be left in position up to 48 hours after the sheep are removed from the area to mop up stray flies.

Mutants. Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage,lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *Bacillus thuringiensis* Isolates

A subculture of a B.t. isolate of the invention can be used to inoculate the following medium, a peptone, glucose, salts medium.

| | |
|---|---|
| Bacto Peptone | 7.50 g/l |
| Glucose | 1.00 g/l |
| $KH_2PO_4$ | 3.40 g/l |
| $K_2HPO_4$ | 4.35 g/l |
| Salt Solution | 5.00 ml/l |
| $CaCl_2$ Solution | 5.00 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 37° C. on a rotary shaker at 200 rpm for 64 hours.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Purification of Protein and Amino Acid Sequencing

The B.t. isolates PS86Q3, PS63B, PS52A1, and PS33F2 were cultured as described in Example 1. The parasporal inclusion bodies were partially purified by sodium bromide (28–38%) isopycnic gradient centrifugation (Pfannenstiel, M. A., E. J. Ross, V. C. Kramer, K. W. Nickerson [1984] *FEMS Miocrobiol Lett.* 21:39). The proteins were bound to PVDF membranes (Millipore, Bedford, Mass.) by western blotting techniques (Towbin, H., T. Staehlelin, K. Gordon [1979] *Proc. Nat. Acad. Sci. USA* 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] *Meth. Enzymol.* 91:399). The sequences obtained were:

86Q3(a): M A T I N E L Y P N V P Y N V L (SEQ ID NO. 1)

63B: Q L Q A Q P L I P Y N V L A (SEQ ID NO. 2)

52A1: M I I D S K T T L P R H S L I N T (SEQ ID NO. 3)

33F2: A T L N E V Y P V N (SEQ ID NO. 4)

In addition, internal amino acid sequence data were derived for 63B. The toxin otein was partially digested with *Staphylococcus aureus* V8 proteasg (Sigma Chem. Co., St. Louis, Mo.) essentially as described (Cleveland, D. W., S. G. Fischer, M. W. Kirschner, U. K. Laemmli [1977] *J. Biol. Chem.* 252:1102). The digested material was blotted onto PVDF membrane and a ca. 28 kDa limit peptide was selected for N-terminal sequencing as described above. The sequence obtained was:

63B(2) V Q R I L D E K L S F Q L I K (SEQ ID NO. 5)

From these sequence data ofigonucleotideprobes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from calliphoricidal B.t. isolates. RFLP analysis of restricted total cellular DNA using radiolabeled oligonucleotide probes has elucidated different genes or gene fragments.

EXAMPLE 3
Restriction Fragment Length Polymorphism (RFLP) Analysis of δ-endotoxin Genes From *Bacillus thuringiensis* strain PS80JJ1

Total cellular DNA was prepared from *Bacillus thuringiensis* (B.t.) cells grown to an optical density, at 600 nm, of 1.0. Cells were pelleted by centrifugation and resuspended in protoplast buffer (20 mg/ml lysozyme in 0.3M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

An approximately 700–800 bp DNA fragment from a novel PS80JJ1 130 kDa toxin gene was obtained by polymerase chain reaction (PCR) amplification using PS80JJ1 cellular DNA and the following primers:

5Q GGACCAGGAT TTACAGG(T or A)GG
(A or G)(A or G)A 3Q (SEQ ID NO. 6)
5Q TAACGTGTAT (A or T)CG(C or
G)TTTTAA TTT(T or A)GA(C or T)TC 3Q
(SEQ ID NO. 7)

This DNA fragment was cloned into pBluescript S/K (Stratagene, LaJolla, Calif.) and partially sequenced by dideoxynucleotide DNA sequencing methodology (Sanger et al. [1977] *Proc. Natl. Acad. Sci. USA* 74:5463–5467) using Sequenase (USBiochemical, Cleveland, Ohio.). DNA sequences unique to at least one PS80JJ1 toxin gene were identified by computer comparison with other known δ-endotoxin genes.

The 700–800 bp DNA fragment was radiolabled with $^{32}P$ and used in standard hybridizations of Southernblots of PS80JJ1 total cellular DNA. Hybridizingbands included an approximately 1.8 kbp EcoRI fragment and an approximately 9.5 kbp HindIII fragment. These hybridizing DNA bands contain toxin genes or restriction fragments of toxin genes from PS80JJ1.

EXAMPLE 4
Molecular Cloning of a Gene Encoding a Toxin from *Bacillus thuringiensis* Strain PS63B Example 2 shows the aminoterrninal and internal polypeptide sequences of the 63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5Q end of the gene:

63B-A-5Q CAA(T or C)TACAAG C(A or T)CAACC 3Q (SEQ ID NO. 8)

The sequence of the reverse primer (63B-INT) was complementary to the inverse of the internal predicted DNA sequence:

63B-INT-5Q TTCATCTAAA ATTCTTTG(A or T)A C 3Q (SEQ ID NO. 9)

These primers were used in standard polymerase chain reactions (Cetus Corporation) to amplify an approximately 460 bp fragment of the 63B toxin gene for use as a DNA cloning probe. Standard Southern blots of total cellular DNA from 63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from *Bacillus thuringiensis* (B.t.) cells grown to an optical density of 1.0 at 600 nm. The cells were recovered by centrifugation and protoplasts were prepared in lysis mix (300 mM sucrose, 25 mM Tris-HCl, 25 mM EDTA, pH 8.0) and lysozyme at a concentration of 20 mg/ml. The protoplasts were ruptured by addition of ten volumes of 0.1M NaCl, 0.1M Tris-HCl pH 8.0, and 0.1% SDS. The cellular material was quickly frozen at −70° C. and thawed to 37° C. twice. The supernatant was extracted twice with phenol/chloroform (1:1). The nucleic acids were precipitated with ethanol. To remove as much RNA as possible from the DNA preparation, RNase at final concentration of 200 µg/ml was added. After incubation at 37° C. for 1 hour, the solution was extracted once with phenol/chloroform and precipitated with ethanol.

A gene library was constructed from 63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (Promega). The packaged phage were plated on *E. coli* KW251 cells (Promega) at a high titer and screened using the radiolabeled approximately 430 bp fragment probe amplified with the 63B-A and 63B internal primers (SEQ ID NOS. 8 and 9, respectively) by polymerase chain reaction. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis, T., E. F. Fritsch, J. Sambrook [1982] *Molecular Cloning: A Laboratory Manual*, Cold Spring Harbor Laboratory, New York). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBlueScript S/K [Stratagene, San Diego, Calif.] and the replication origin from a resident B.t. plasmid [Lereclus, D. et al. (1989) *FEMS Microbiol. Lett.* 60:211–218]). The ligation mix was introduced by transformation into competent *E. coli* NM522 cells (ATCC 47000) and plated on LB agar containing ampicillin (100 μg/ml), isopropyl-β-D-thiogalactoside (IPTG) (2%), and 5-bromo-4-chloro-3-indolyl-β-D-galactoside (XGAL) (2%). White colonies, with putative restriction fragment insertions in the β-galactosidase gene of pHTBlueII, were subjected to standard rapid plasmid purification procedures (Maniatis et al., supra). Plasmids were analyzed by SalI digestion and agarose gel electrophoresis. The desired plasmid construct, pMYC1641, contains an approximately 14 kb SalI insert.

For subcloning, preparative amounts of DNA were digested with xbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 5
Molecular Cloning of a Toxin Gene From *B.t.* PS33F2 and Transformation into *Escherichia coli*

Total cellular DNA was prepared from *Bacillus thuringiensis* PS33F2 (*B.t.* PS33F2) as described above in Example 3.

Plasmid DNA was extracted from protoplasts prepared by incubation of cells for 1 hour at 37° C. in protoplast buffer (20 mg/ml lysozyme in 0.3M sucrose, 25 mM Tris-HCl [pH 8.0], 25 mM EDTA). Protoplasts were lysed by the addition of nine volumes of a solution of 10 mM Tris-Cl, 1 mM EDTA, 0.085N NaOH, 0.1% SDS, pH 8.0. SDS was added to 1% final concentration to complete lysis. One-half volume of 3M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}$P-labelled oligonucleotide probes designed to the N-terminal amino acid sequence disclosed in Example 2.

Probe 33F2A: 5Q GC(A or T)AC(A or T)TTAA ATGAAGT(A or T)TA T 3Q (SEQ ID NO. 10).

Probe 33F2B: 5Q AATGAAGT(A or T)T ATCC(A or T)GT(A or T)AA T 3Q (SEQ ID NO. 11).

Hybridizing bands included an approximately 5.85 kbp EcoRI fragment. Probe 33F2A and a reverse PCR primer were used to amplify a DNA fragment of approximately 1.8 kbp for use as a hybridization probe for cloning the 33F2 toxin gene. The sequence of the reverse primer was:

5Q GCAAGCGGCC GCTTATGGAA TAAATTCAAT T(C or T)(T or G)(A or G)TC(T or A)A 3Q (SEQ ID NO. 12).

A gene library was constructed from 33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene N.H.). The EcoRI inserts were ligated into EcoRI-digested pHTBlueII (an *E. coli*/*B. thuringiensis* shuttle vector comprised of pBluescript S/K [Stratagene] and the replication origin from a resident *B.t.* plasmid (Lereclus et al., supra]). The ligation mixture was transformed into frozen, competent NM522 cells (ATCC 47000). Tranformants were plated on LB agar containing ampicillin, IPTG, and XGAL. Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33 F2a) is novel compared to the DNA sequences of other toxin genes encoding pesticidal proteins.

Plasmid pMYC2316 was introduced into the acrystalliferous (Cry-) *B.t.* host, HD-1 CryB (A. Aronson, Purdue University, West Lafayette, Ind.) by electroporation. Expression of an approximately 120–140 kDa crystal protein was verified by SDS-PAGE analysis. Crystals were purified on NaBr gradients (Pfannenstiel et al., supra).

EXAMPLE 6

Molecular Cloning and Expression of a Toxin Gene from *B.t.* Isolate PS86Q3

Total cellular DNA was prepared from *Bacillus thuringiensis* PS86Q3 (*B.t.* PS86Q3) as disclosed above in Example 3.

Total cellular DNA from isolate PS86Q3 was used as template for polymerase chain reaction (PCR) analysis according to protocols furmished by Perkin Elmer Cetus. An oligonucleotide derived from the N-terminal amino acid sequence of the toxin protein was used as a 5Q primer. The sequence of this oligonucleotide is: 5Q-AGACTGGATC CATGGC(A or T)AC(A or T) AT(A or T)AATGAAT TATA(T or C)CC-3Q (SEQ ID NO. 13).

An oligonucleotide coding for the amino acid sequence "ESKLKPNTRY" (SEQ ID NO. 14) can be used as the reverse 3Q primer. The sequence of this oligonucleotide can be: "5Q-TAACGTGTAT (A or T)CG(C or G)TTTTAA TTT(T or A)GA(C or T)TC-3Q" (SEQ ID NO. 15).

The oligonucleotidecoding for the amino acid sequence "YIDKIEFIP" (SEQ ID NO. 16) was also used as a reverse 3Q primer in conjunction with the above mentioned 5Q primer. The sequence of the reverse primer can be: "5Q-TGGAATAAAT TCAATT(C or T)(T or G)(A or G)T C(T or A)A-3Q" (SEQ ID NO. 17).

Amplification with the 5Q primer and SEQ ID NO. 15 generates an approximately 2.3 kbp DNA fragment and an approximately 4.3 kbp DNA fragment. Amplification with the 5Q primer and SEQ ID NO. 17 generates an approximate 1.8 kbp DNA fragment and an approximately 3.7 kbp DNA fragment. The approximately 2.3 kbp fragment was radiolabeled with $^{32}$P and used as a hybridization probe to generate restriction fragment polymorphism (RFLP) patterns and to screen recombinant phage libraries.

A Southern blot of total cellular DNA digested with EcoRV was probed with the radiolabeled 2.3 kbp probe described above. The resultant RFLP includes 9.5 kbp, 6.4 kbp, and 4.5 kbp hybridizing fragments.

A gene library was constructed from PS86Q3 total cellular DNA partially digested with NdeII and size fractioned by gel electrophoresis. The 9–23 kb region of the gel was excised and the DNA was electroeluted and then concentrated using an Elutip-D ion exchange column (Schleicher and Schuel, Keene, N.H.). The isolated NdeII fragments were ligated into BamHI-digested LambdaGem-11 (Promega). The packaged phage were plated on *E. coli* KW251 cells (Promega) at a high titer and screened using the radiolabeled probe described above. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis et al., supra). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B.t.* shuttle vector comprised of pBluescript S/K [Stratagene, San Diego, Calif.]) and the replication origin from a resident *B.t.* plasmid (Lereclus et al., supra). The ligation mix was introduced by transformation into competent *E. coli* NM522 cells (ATCC 47000) and plated on LB agar containing ampicillin, IPTG and XGAL. White colonies, with putative restriction fragment insertions in the β-galactosidase gene of pHTBlueII, were subjected to standard rapid plasmid purification procedures (Maniatis et al., supra). Plasmid DNA was analyzed by SalI digestion and agarose gel electrophoresis. The desired plasmid construct, pMYC1647, contains an approximately 12 kb SalI insert. Plasmid pMYC1647 was introduced by electroporation into an acrystalliferous (Cry⁻) *B.t.*, HD-1 CryB (A. I. Aronson, Purdue University) host to yield MR515, a recombinant *B.t.* clone of 86Q3(a). Expression of an approximately 155 kDa protein was verified by SDS-PAGE. Spores and crystals can be removed from broth cultures and used for determination of pesticidal activity.

EXAMPLE 7

Molecular Cloning and Expression of a Toxin Gene From *Bacillus thuringiensis* strain PS52A1

Total cellular DNA was prepared from *Bacillus thuringiensis* PS52A 1 (*B.t.* PS52A1) as disclosed above in Example 3.

RFLP analyses were performed by standard hybridization of Southern blots of PS52A 1 DNA with a $^{32}$P-labeled oligonucleotide probe designed from the N-terminal amino acid sequence disclosed in Example 2. The sequence of this probe is:

5Q ATGATTATTG ATTCTAAAAC AACATTACCA AGACATTC(A or T)T TAAT(A or T)AATAC (A or T)AT(A or T)AA 3Q (SEQ ID NO. 18).

This probe was designated 52A1-C. Hybridizing bands included an approximately 3.6 kbp HindIII fragment and an approximately 8.6 kbp EcoRV fragment. A gene library was constructed from PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega). Recombinant phage were packaged and plated on *E. coli* KW251 cells (Promega). Plaques were screened by hybridization with the radiolabeled 52A1-C oligonucleotide probe disclosed above. Hybridizing phage were plaque-purified and used to infect liquid cultures of *E. coli* KW251 cells for isolation of phage DNA by standard procedures (Maniatis et al, supra). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI+SalI-digested pHTBlueII (an *E. coli/B. thuringiensis* shuttle vector comprised of pBluescript S/K [Stratagene] and the replication origin from a resident *B.t.* plasmid [Lereclus et al., supra]). The ligation mix was used to transform frozen, competent *E. coli* NM522 cells (ATCC 47000). Transformants were plated on LB agar containing ampicillin, IPTG, and XGAL. Plasmids were purified from putative recombinants by alkaline lysis (Maniatis et al, supra) and analyzed by electrophoresis of EcoRI and SalI digests on agarose gels. The desired plasmid construct, pMYC2321 contains a toxin gene that is novel compared to the maps of other toxin genes.

Plasmid pMYC2321 was introduced into an acrystalliferous (Cry⁻) *B.t.* host by electroporation. Expression of an approximately 55–60 kDa crystal protein was verified by SDS-PAGE analysis.

EXAMPLE 8

Molecular Cloning and Expression of a Toxin Gene from *Bacillus thuringiensis* Strain PS91C2

Total cellular DNA was prepared from *Bacillus thuringiensis* PS91C2 (*B.t.* PS91C2) as disclosed above in Example 3.

A 1.58 kbp fragment of the novel 130 kDa toxin gene was obtained by polymerase chain reaction (PCR) amplification from PS91C2 cellular DNA using the following primers: "Forward" 5Q-GAGTGGGAAGCAGATCTTAATAATG-CACAATTAAGG-3Q(SEQ ID NO. 19); "Reverse" 5Q-ATAC(C or T)CGATC GATATGATA(G or A) TCCGT-3Q (SEQ ID NO. 20). This DNA fragment was cloned into pBluescript S/K (Stratagene, La Jolla, Calif.) and the DNA sequence determined by dideoxynucleotide sequencing methodology (Sanger et al., supra) using Sequenase (US Biochemicals, Cleveland, Ohio). DNA sequences that were unique were identified by computer comparison with other toxin genes. An oligonucleotide probe with the following sequence was synthesized: 5Q-CCCAATGTGA ATGTACTTTGCGC-3Q(SEQ ID NO. 21). This probe was radiolabelled with $^{32}$P and used in standard hybridizations of Southern blots of PS91C2 total cellular DNA. Hybridizing bands included an approximately 7.5 kbp HindIII fragment.

A gene library was constructed from PS91C2 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with each of the respective probes described above. Hybridizing phage were plaque purified and used to infect liquid cultures of *E. coli* KW251 cells for isolation of DNA by standard procedures (Maniatis et al., supra).

For subcloning the gene encoding the 130 kDa toxin, preparative amounts of phage DNA were digested with SauI and electrophoresed on an agarose gel. The approximately 8 kbp bad containing the toxin gene was excised from the gel electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K (Stratagene, La Jolla, Calif.) and the replication origin from a resident *B.t.* plasmid (Lereclus et al., supra). The ligation mix was used to transform frozen, competent *E. coli* NM522 cells (ATCC 47000). β-galactosidase transformants were screened by restriction digestion of alkaline lysate plasmid minipreps as above. The desired plasmid construct, pMYC2361, contains a toxin gene that is novel compared to other toxin genes containing insecticidal proteins.

pMYC2361 was introduced into the acrystalliferous (Cry⁻) *B.t.* host. CryB (A. Aronson, Purdue University, West Lafayette, Ind.), by electroporation. expression of the 130 kDa toxin was demonstrated by SDS-PAGE analysis. NaBr-purified crystals were prepared (Pfannenstiel et al., supra).

EXAMPLE 9
Molecular Cloning and Expression of Toxin Genes from *Bacillus thuringiensis* Strain PS201T6

Total cellular DNA was prepared from *Bacillus thuringiensis* PS201T6 (*B.t.* PS201T6) as described above in Example 3.

RFLP analyses were performed by standard hybridization of Southern blots of PS201T6 DNA digested with various restriction endonucleases. An oligonucleotide probe deduced from the amino acid sequence of the 30 kDa toxin was used to detect the gene encoding this polypeptide. The sequence of this probe was: 5Q-GACTGGATCC ATGAAAGAA(T or A) (G or C)(T or A)AT(T or A)TATTA TAATGAAGA-3Q (SEQ ID NO. 22). This probe was mixed at four positions and contained a 5Q BamHI cloning site. Hybridizing bands included an approximately 4.0 kbp EcoRI fragment and an approximately 2.7 kbp EcoRV fragment.

A 285 bp probe for detection of the 130 kDa toxin gene was obtained by polymerase chain reaction (PCR) amplification from 201T6 cellular DNA using the *B.t.* universal forward and YIDKIEFIP reverse oligonucleotide primers (SEQ ID NOS. 23 and 17, respectively). The sequence of the *B.t.* universal primer is: 5Q-GGACCAGGAT TTACAG-GAGG AGAT-3Q (SEQ ID NO. 23). The amplified DNA fragment was radiolabelled with $^{32}$P-dATP using a BMB (Indianapolis, Ind.) random priming kit. Southern blot analyses of PS201T6 DNA with this probe revealed hybridizing bands that included an approximately 9.3 kbp HindIII fragment and two EcoRI fragments approximately 1.8 and 4.5 kbp in size.

A gene library was constructed from PS201T6 DNA partially digested with Sau3A. Partial restriction digests were fractionated by agarose gel electrophoresis. DNA fragments 9.3 to 23 kbp in size were excised from the gel, electroeluted from the gel slice, purified on an Elutip D ion exchange column (Schleicher and Schuell, Keene, N.H.), and recovered by ethanol precipitation. The Sau3A inserts were ligated into BamHI-digested LambdaGem-11 (Promega, Madison, Wis.). Recombinantphage were packaged and plated on *E. coli* KW251 cells. Plaques were screened by hybridization with each of the respective probes described above. Hybridizing phage were plaque purified and used to infect liquid cultures of *E. coli* KW251 cells for isolation of DNA by standard procedures (Maniatis et al., supra).

For subcloning the gene encoding the 30 kDa toxin gene, preparative amounts of phage DNA were digested with EcoRI and electrophoresed on an agarose gel. The approximately 4.5 kbp band containing the toxin gene was excised from the gel electroeluted from the gel slice, and purified by ion exchange chromatography as above. The purified DNA insert was ligated into EcoRI-digested pBluescript K/S (Stratagene, La Jolla, Calif.). The ligation mix was used to transform frozen, competent *E. coli* NM522 cells (ATCC 47000). Transformants were plated on LB agar containing 100 μg/ml ampicillin, 1 mM IPTG, and 0.5 mM XGAL. Plasmids were purified from putative recombinants by alkaline lysis (Maniatis et al., supra) and analyzed by restriction endonuclease digestion and agarose gel electrophoresis. The desired plasmid construct pMYC2357 contains a toxin gene that is novel compared to other toxin genes encoding insecticidal proteins.

The gene encoding the 30 kDa was expressed under control of the p52A1 promoter and ribosome binding site in the vector, pBClac (an *E. coli/B. thuringiensis* shuttle vector comprised of the replication origin from pBC16 (Bernhard, K. et al. [1978] *J. Bacteriol.* 133:897–903)and pUC19 (Yanisch-Perron, C. et al. [1985] *Gene* 33:103–119). The 30 kDa open reading frame and 3Q flanking sequences were amplified by PCR using a forward oligonucleotide complementary to the 5Q end of the gene and a reverse oligonucleotide complementary to the T7 promoter region of pBluescript. The sequence of the gene-specific primer was: 5Q-GGAATTCCTC ATG AAA GAG TCA ATT TAC TAC A-3Q (SEQ ID NO. 24). This primer contained a 5Q BspHI cloning site. The p52A1 promoter/rbs sequences were amplified using a promoter-specific primer and a vector primer from pMYC2321. The sequence of promoter-specific primer was 5Q-GTAAACATGT TCATACCACC TTTTTAA-3Q (SEQ ID NO. 25). This primer contained a 5Q AflIII cloning site. The p52A1 promoter fragment (digested with BamHI and AflIII), the 30 kDa toxin gene fragment (digested with BspHI and SalI) and pBClac (digested with BamHI and SalI) were ligated together to generate pMYC2358. This construct was introduced into the acrystalliferous (Cry$^-$) *B.t.* host, CryB (A. Aronson, Purdue University, West Lafayette, Ind.) by electroporation. Expression of the 30 kDa toxin was demonstrated by SDS-PAGE analysis. NaBr-purified crystals were prepared (Pfannenstiel et al., supra).

For subcloning the 130 kDa toxin, preparative amounts of phage DNA were digested with SalI and electrophoresed on an agarose gel. The approximately 12.8 kbp band containing the toxin gene was excised from the gel, electroeluted from the gel slice, and purified by ion exchange chromatography as described above. The purified DNA insert was ligated into an XhoI-digested pHTBlueII (an *E. coli/B. thuringiensis* shuttle vector comprised of pBluescript S/K (Stratagene, La Jolla, Calif.) and the replication origin from a resident *B.t.* plasmid (Lereclus et al., supra). The ligation mix was used to transform frozen, competent *E. coli* NM522 cells (ATCC 47000). β-galactosidase transformants were screened by restriction digestion of alkaline lysate plasmid minipreps as above. The desired plasmid construct, pMYC2362, contains a toxin gene that is novel compared to other toxin genes encoding pesticidal proteins.

pMYC2362 was introduced into the acrystalliferous (Cry$^-$) *B.t.* host, CryB (A. Aronson, Purdue University, West Lafayette, Ind.), by electroporation. Expression of the 130 kDa toxin was demonstrated by SDS-PAGE analysis.

EXAMPLE 10
Cloning of ≈130 kDa Toxin Gene from Isolate *B.t.* PS71M3 and Transformation into *Escherichia coli*

Total cellular DNA was prepared from *B.t.* cells grown to a low optical density (OD$_{600}$=1.0). The cells were recovered by centrifugation and protoplasted in TES buffer (30 mM Tris-Cl, 10 mM ethylenediaminetetraacetic acid [EDTA], 50 mM NaCl, pH 8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from *B.t.* PS71M3 was digested with EcoRV and separated by electrophoresis on a 0.8% (w/v) Agarose-TAE (50 mM Tris-Cl, 20 mM NaOAc, 2.5 mM EDTA, pH 8.0) buffered gel. A Southern blot of the gel was hybridized with a [$^{32}$P] radiolabeled probe. The sequence of the oligonucleotide is GGTGATTTTA CACAAGGGGT AATGGGGTGG CATG (SEQ ID NO. 26). Results showed that the hybridizing fragments of B.t. PS71M3 are 4.8 kb, 4.0 kb, and 3.8 kb in size.

A library was constructed from B.t. PS71M3 total cellular DNA partially digested with Sau3A and size fractionated by electrophoresis. The 9 to 23 kb region of the gel was excised and the DNA was electroeluted and then concentrated using an Elutip ion exchange column (Scleicher and Schuel, Keene, N.H.). The isolated Sau3A fragments were ligated into LambdaGem-11 (Promega). The packaged phage were plated on KW251 E. coli cells (Promega) at a high titer and screened using the radiolabeled synthetic oligonucleotide as a nucleic acid hybridization probe. Hybridizing plaques were purified and rescreened at a lower plaque density. Single isolated purified plaques that hybridized with the probe were used to infect KW251 E. coli cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligatedto SalI-digestedand dephosphorylated pBClac. The ligation mix was introduced by transformation into NM522 competent E. coli cells and plated on LB agar containing ampicillin, IPTG and XGAL. White colonies, with putative insertions in the β-galactosidase gene of pBClac, were subjected to standard rapid plasmid purification procedures to isolate the desired plasmid. The selected plasmid was named pMYC1625 and contains an 8.0 kb SalI insert.

The toxin gene was sequenced by the standard Sanger dideoxy chain termination method using oligonucleotideprimers made to the B.t.i. cryIVA gene and by "walking" with primers made to the sequence of the new toxin gene. Sequence analysis of the toxin gene revealed that it encodes a protein of 134,934 daltons, deduced from the DNA sequence. The nucleotide and deduced amino acid sequences are shown in SEQ ID NOS. 27 and 28, respectively.

Plasmid pMYC1625 was introduced into a cured, acrystalliferous(Cry−) B.t. host by electroporation. Expression of an ≈130 kD protein was verified by SDS-PAGE. Spores and crystals were used for the determination of toxicity to calliphorids.

The pBClac shuttle vector was constructed by fusing plasmids pBC 16-1 (Bacillus Genetic Stock Center, Ohio State University, Department of Biochemistry, Columbus, Ohio) and pUC19 (New England Biolabs). The pBC16-1 plasmid was digested with EcoRI and the 5Q overhangs were filled in with deoxynucleotides (dATP, dCTP, dGTP, and dTTP) by Klenow enzyme (New England Biolabs). An SpeI restriction site was added by ligation of oligonucleotide linkers forming pBC16-1SpeI. In the same manner as above, an NheI restriction site was added to pUC19 at the Eco0109 site forming pUC19NheI. The pBC16-1SpeI plasmid was digested with SpeI and the pUC19NheI plasmid was digested with NheI, creating complementary cohesive ends that were ligated together to form the pBClac shuttle vector.

The plasmid containing the B.t. toxin gene can be removed from the transformed host microbe by use of standard well-known procedures. For example, the host microbe can be subjected to cleared lysate isopycnic density gradient procedures, and the like, to recover the desired plasmid.

The above gene can also be isolated from B.t. PS71M3-69 by the same procedures.

EXAMPLE 11
Cloning of ≈77 kDa Toxin Gene From Isolate B.t. PS71M3 and Transformation into *Escherichia coli*

As described in Example 10, total cellular DNA was prepared. Total cellular DNA from B.t. PS71M3 was digested with EcoRV and separated by electrophoresis on a 0.8% (w/v) agarose-TAE (50 mM Tris-HCl, 20 mM NaOAc, 2.5 mM EDTA, ph=8.0) buffered gel. A Southern blot of the gel was hybridized with a [$^{32}$P]-radiolabeled oligonucleotide probe. The sequence of the oligonucleotide is CCAAGGGCGTTTTTACACAA GAAATTCTCG AGAC (SEQ ID NO. 29). Results showed that the hybridizing fragments of B.t. PS71M3 are approximately 14.0 kb and 2.9 kb in size.

A library was constructed as described in Example 10. White colonies, with putative insertions in the β-galactosidase gene of pBClac, were subjected to standard rapid plasmid purification procedures to isolate the desired plasmid. The selected plasmid was named pMYC1636 and contains an approximately 15 kb SalI insert.

The restriction map of the cloned insert indicates that the toxin gene is novel compared to the maps of other toxin genes encoding calliphoricidal proteins.

The toxin gene was sequenced by the standard dideoxy chain termination method using oligonucleotide primers made to the B.t.i. cryIVC gene and by "walking" with primers made to the sequence of the new toxin gene. Sequence analysis of the toxin gene revealed an open reading frame that is ≈95% homologous to the cryIVC gene, and encodes a protein of 77,798 daltons, deduced from the DNA sequence, that has 2 different amino acids. The nucleotide and deduced amino acid sequences are shown in SEQ ID NOS. 30 and 31, respectively.

Plasmid pMYC1636 was introduced into an acrystalliferous (cry−) B.t. host by electroporation. Expression of an approximately 68 kD processed protein was verified by SDS-PAGE.

EXAMPLE 12
Insertion of Toxin Genes Into Plants

One aspect of the subject invention is the transformation of plants with genes encoding a calliphorid toxin. The transformed plants are resistant to attack by calliphorids.

Genes encoding calliphorid-active toxins, as disclosed herein, can be inserted into plant cells using a variety of techniques which are well known in the art. For example, a large number of cloning vectors comprising a replication system in E. coli and a marker that permits selection of the transformed cells are available for preparation for the insertion of foreign genes into higher plants. The vectors comprise, for example, pBR322, pUC series, M13mp series, pACYC184, etc. Accordingly, the sequence encoding the B.t. toxin can be inserted into the vector at a suitable restriction site. The resulting plasmid is used for transformation into E. coli. The E. coli cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteriaare used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacteriumused as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 13
Cloning of Novel *B.t.* Genes Into Insect Viruses

A number of viruses are known to infect insects. These viruses include, for example, baculoviruses and entomopoxviruses. In one embodiment of the subject invention, calliphorid-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

EXAMPLE 14
Activity Against Blowfly Pests

A technical powder containing 30% biomass was prepared. The powder was mixed with newborn calf serum to a concentration of 50,000 ppm. Dental plugs were saturated with the solution. Newly hatched sheep blowfly maggots were exposed to the saturated plugs. Maggot mortality was assessed 24 and 48 hours after initial exposure.

TABLE 4

| B.t. Strain | Percent Mortality |
|---|---|
| PS123D1 | 98.5 |
| PS71M3 | 99.5 |
| PS63B2 | 95.0 |
| PS52A1 | 98.5 |
| PS80JJ1 | 99.5 |
| PS204G6 | 97.5 |
| PS91C2 | 80.0 |
| PS173A | 100.0 |
| PS31J2 | 87.5 |
| PS201T6 | 100.0 |
| PS86Q3 | 97.5 |
| PS7401 | 100.0 |
| PS33F2 | 95.0 |
| PS202U2 | 90.0 |
| PS83E5 | 99.5 |
| PS84C3 | 95.0 |
| PS204C3 | 80.0 |
| PS207B6 | 90.0 |
| PS211B2 | 94.0 |
| Control | 4.0 |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling pests of the family Calliphoridae, which comprises contacting said pests with a calliphorid-controlling amount of a *Bacillus thuringiensis* microbe *B.t.* PS31J2 or a toxin from said microbe.

2. The method, according to claim 1, wherein said pest is selected from the group consisting of blowflies and screwworms.

3. The method, according to claim 1, which further comprises administration of one or more additional calliphorid-controlling compounds.

4. The method, according to claim 1, wherein said toxin is administered as a drench.

5. The method, according to claim 1, wherein said toxin is administered in a bait bin.

6. A composition of matter for controlling pests of the family Calliphoridae comprising a *Bacillus thuringiensis* microbe *B.t.* PS31J2 or a toxin from said microbe, in association with a carrier particularly suited for use in treating calliphorids.

7. The composition, according to claim 6, which further comprises one or more additional calliphorid-controlling compounds.

8. A biologically pure culture of *Bacillus thuringiensis* PS31J2.

* * * * *

UNITED STATES PATENT AND TRADEMARK OFFICE
CERTIFICATE OF CORRECTION

Page 1 of 2

PATENT NO. : 5,888,503
DATED : March 30, 1999
INVENTOR(S) : Leslie A. Hickle, et. al.

It is certified that error appears in the above-identified patent and that said Letters Patent is hereby corrected as shown below:

Column 1, line 24: "endotoxingenes" should read --endotoxin genes--.

Column 4, line 40: "oligonucleotideprimer" should read --oligonucleotide primer--.

Column 6, line 65: "calliphoridactive" should read --calliphorid-active--.

Column 10, line 8: "constructprovides" should read --construct provides--.

Column 12, line 62: "otein" should read --protein--.

Column 12, line 63: "proteasg" should read --protease--.

Column 13, line 4: "ofigonucleotideprobes" should read --oligonucleotide probes--

Column 13, line 59: "Hybridizingbands" should read --Hybridizing bands--.

Column 14, line 1: "aminoterminal" should read --aminoterminal--.

Column 14, line 6: "6-endotoxins" should read --δ-endotoxins--.

Column 15, line 12: "xbaI" should read --XbaI--.

Column 16, line 34: "oligonucleotidecoding" should read --oligonucleotide coding--.

Column 18, line 29: "oligonucleotideprobe" should read --oligonucleotide probe--..

Column 19, line 1: "expression" should read --Expression--.

UNITED STATES PATENT AND TRADEMARK OFFICE
CERTIFICATE OF CORRECTION

PATENT NO. : 5,888,503
DATED : March 30, 1999
INVENTOR(S) : Leslie A. Hickle, et. al.

It is certified that error appears in the above-identified patent and that said Letters Patent is hereby corrected as shown below:

Column 19, line 42: "Recombinantphage" should read --Recombinant phage--.

Column 21, line 21: "ligatedto" should read --ligated to--.

Column 21, line 22: "digestedand" should read --digested and--.

Column 21, lines 30-31: "oligonucleotidep-rimers" should read --oligonucleotide primers--.

Column 23, line 19: "agrobacteriaare" should read --agrobacteria are--.

Column 23, line 35: "agrobacteriumused" should read --agrobacterium used--.

Column 24, line 41: "PS7401" should read --PS74G1--.

Signed and Sealed this

Twenty-fourth Day of October, 2000

Attest:

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:1:

Met Ala Thr Ile Asn Glu Leu Tyr Pro Asn Val Pro Tyr Asn Val Leu
1               5                   10                  15

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Gln Leu Gln Ala Gln Pro Leu Ile Pro Tyr Asn Val Leu Ala
1               5                   10

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Met Ile Ile Asp Ser Lys Thr Thr Leu Pro Arg His Ser Leu Ile Asn
1               5                   10                  15

Thr ( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Ala Thr Leu Asn Glu Val Tyr Pro Val Asn
1               5                   10

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

Val Gln Arg Ile Leu Asp Glu Lys Leu Ser Phe Gln Leu Ile Lys
1               5                   10                  15

( 2 ) INFORMATION FOR SEQ ID NO:6:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

GGACCAGGAT TTACAGGWGG RRA        23

( 2 ) INFORMATION FOR SEQ ID NO:7:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

TAACGTGTAT WCGSTTTTAA TTTWGAYTC        29

( 2 ) INFORMATION FOR SEQ ID NO:8:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

CAAYTACAAG CWCAACC        17

( 2 ) INFORMATION FOR SEQ ID NO:9:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

TTCATCTAAA ATTCTTTGWA C        21

( 2 ) INFORMATION FOR SEQ ID NO:10:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

GCWACWTTAA ATGAAGTWTA T        21

( 2 ) INFORMATION FOR SEQ ID NO:11:

( i ) SEQUENCE CHARACTERISTICS:
        ( A ) LENGTH: 21 bases
        ( B ) TYPE: nucleic acid ( C ) STRANDEDNESS: single
( D ) TOPOLOGY: linear ( i i ) MOLECULE TYPE: DNA (synthetic)

( x i ) SEQUENCE DESCRIPTION: SEQ ID NO:11:

AATGAAGTWT ATCCWGTWAA T                                                                21

( 2 ) INFORMATION FOR SEQ ID NO:12:

( i ) SEQUENCE CHARACTERISTICS:
( A ) LENGTH: 38 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:12:

GCAAGCGGCC GCTTATGGAA TAAATTCAAT TYKRTCWA                                               38

( 2 ) INFORMATION FOR SEQ ID NO:13:

( i ) SEQUENCE CHARACTERISTICS:
( A ) LENGTH: 37 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:13:

AGACTGGATC CATGGCWACW ATWAATGAAT TATAYCC                                                37

( 2 ) INFORMATION FOR SEQ ID NO:14:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

Glu  Ser  Lys  Leu  Lys  Pro  Asn  Thr  Arg  Tyr
1                   5                             10

( 2 ) INFORMATION FOR SEQ ID NO:15:

( i ) SEQUENCE CHARACTERISTICS:
( A ) LENGTH: 29 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:15:

TAACGTGTAT WCGSTTTTAA TTTWGAYTC                                                         29

( 2 ) INFORMATION FOR SEQ ID NO:16:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:16:

Tyr Ile Asp Lys Ile Glu Phe Ile Pro
1               5

( 2 ) INFORMATION FOR SEQ ID NO:17:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:17:

TGGAATAAAT TCAATTYKRT CWA                                                    23

( 2 ) INFORMATION FOR SEQ ID NO:18:

( i ) SEQUENCE CHARACTERISTICS:
    ( A ) LENGTH: 56 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:18:

ATGATTATTG ATTCTAAAAC AACATTACCA AGACATTCWT TAATWAATAC WATWAA                56

( 2 ) INFORMATION FOR SEQ ID NO:19:

( i ) SEQUENCE CHARACTERISTICS:
    ( A ) LENGTH: 36 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:19:

GAGTGGGAAG CAGATCTTAA TAATGCACAA TTAAGG                                      36

( 2 ) INFORMATION FOR SEQ ID NO:20:

( i ) SEQUENCE CHARACTERISTICS:
    ( A ) LENGTH: 25 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:20:

ATACYCGATC GATATGATAR TCCGT                                                  25

( 2 ) INFORMATION FOR SEQ ID NO:21:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:21:

CCCAATGTGA ATGTACTTTG CGC                                                    23

( 2 ) INFORMATION FOR SEQ ID NO:22:

( i ) SEQUENCE CHARACTERISTICS:
    ( A ) LENGTH: 39 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:22:

GACTGGATCC ATGAAAGAAW SWATWTATTA TAATGAAGA      39

( 2 ) INFORMATION FOR SEQ ID NO:23:

( i ) SEQUENCE CHARACTERISTICS:
    ( A ) LENGTH: 24 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:23:

GGACCAGGAT TTACAGGAGG AGAT      24

( 2 ) INFORMATION FOR SEQ ID NO:24:

( i ) SEQUENCE CHARACTERISTICS:
    ( A ) LENGTH: 31 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:24:

GGAATTCCTC ATGAAAGAGT CAATTTACTA C      31

( 2 ) INFORMATION FOR SEQ ID NO:25:

( i ) SEQUENCE CHARACTERISTICS:
    ( A ) LENGTH: 27 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:25:

GTAAACATGT TCATACCACC TTTTTAA      27

( 2 ) INFORMATION FOR SEQ ID NO:26:

( i ) SEQUENCE CHARACTERISTICS:
    ( A ) LENGTH: 34 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:26:

GGTGATTTTA CACAAGGGGT AATGGGGTGG CATG      34

( 2 ) INFORMATION FOR SEQ ID NO:27:

( i ) SEQUENCE CHARACTERISTICS:

(A) LENGTH: 3543 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

| | | | | | | |
|---|---|---|---|---|---|---|
| ATGAATCCTT | ATCAAAATAA | AAATGAATAT | GAAACATTAA | ATGCTTCACA | AAAAAAATTA | 60 |
| AATATATCTA | ATAATTATAC | AAGATATCCA | ATAGAAAATA | GTCCAAAACA | ATTATTACAA | 120 |
| AGTACAAATT | ATAAGATTG | GCTCAATATG | TGTCAACAGA | ATCAGCAGTA | TGGTGGAGAT | 180 |
| TTTGAAACTT | TTATTGATAG | TGGTGAACTC | AGTGCCTATA | CTATTGTAGT | TGGGACCGTA | 240 |
| CTGACTGGTT | TCGGGTTCAC | AACACCCTTA | GGACTTGCTT | TAATAGGTTT | TGGTACATTA | 300 |
| ATACCAGTTC | TTTTTCCAGC | CCAAGACCAA | TCTAACACAT | GGAGTGACTT | TATAACACAA | 360 |
| ACTAAAAATA | TTATAAAAAA | AGAAATAGCA | TCAACATATA | TAAGTAATGC | TAATAAAATT | 420 |
| TTAAACAGGT | CGTTTAATGT | TATCAGCACT | TATCATAATC | ACCTTAAAAC | ATGGGAGAAT | 480 |
| AATCCAAACC | CACAAAATAC | TCAGGATGTA | AGGACACAAA | TCCAGCTAGT | TCATTACCAT | 540 |
| TTTCAAAATG | TCATTCCAGA | GCTTGTAAAC | TCTTGTCCTC | CTAATCCTAG | TGATTGCGAT | 600 |
| TACTATAACA | TACTAGTATT | ATCTAGTTAT | GCACAAGCAG | CAAACTTACA | TCTGACTGTA | 660 |
| TTAAATCAAG | CCGTCAAATT | TGAAGCGTAT | TTAAAAAACA | ATCGACAATT | CGATTATTTA | 720 |
| GAGCCTTTGC | CAACAGCAAT | TGATTATTAT | CCAGTATTGA | CTAAAGCTAT | AGAAGATTAC | 780 |
| ACTAATTATT | GTGTAACAAC | TTATAAAAAA | GGATTAAATT | TAATTAAAAC | GACGCCTGAT | 840 |
| AGTAATCTTG | ATGGAAATAT | AAACTGGAAC | ACATACAATA | CGTATCGAAC | AAAAATGACT | 900 |
| ACTGCTGTAT | TAGATCTTGT | TGCACTCTTT | CCTAATTATG | ATGTAGGTAA | ATATCCAATA | 960 |
| GGTGTCCAAT | CTGAACTTAC | TCGAGAAATT | TATCAGGTAC | TTAACTTCGA | AGAAAGCCCC | 1020 |
| TATAAATATT | ATGACTTTCA | ATATCAAGAG | GATTCACTTA | CACGTAGACC | GCATTTATTT | 1080 |
| ACTTGGCTTG | ATTCTTTGAA | TTTTTATGAA | AAAGCGCAAA | CTACTCCTAA | TAATTTTTTC | 1140 |
| ACCAGCCATT | ATAATATGTT | TCATTACACA | CTTGATAATA | TATCCCAAAA | ATCTAGTGTT | 1200 |
| TTTGGAAATC | ACAATGTAAC | TGATAAATTA | AAATCTCTTG | GTTTGGCAAC | AAATATTTAT | 1260 |
| ATTTTTTTAT | TAAATGTCAT | AAGCTTAGAT | AATAAATATC | TAAATGATTA | TAATAATATT | 1320 |
| AGTAAAATGG | ATTTTTTTAT | AACTAATGGT | ACTAGACTTT | TGGAGAAAGA | ACTTACAGCA | 1380 |
| GGATCTGGGC | AAATAACTTA | TGATGTAAAT | AAAAATATTT | TCGGGTTACC | AATTCTTAAA | 1440 |
| CCAAGAGAGA | ATCAAGCAAT | CCCTACCCTT | TTTCCAACAT | ATGATAACTA | TAGTCATATT | 1500 |
| TTATCATTTA | TTAAAAGTCT | TAGTATCCCT | GCAACATATA | AAACTCAAGT | GTATACGTTT | 1560 |
| GCTTGGACAC | ACTCTAGTGT | TGATCCTAAA | AATACAATTT | ATACACATTT | AACTACCCAA | 1620 |
| ATTCCAGCTG | TAAAAGCGAA | TTCACTTGGG | ACTGCTTCTA | AGGTTGTTCA | AGGACCTGGT | 1680 |
| CATACAGGAG | GGGATTTAAT | TGATTTCAAA | GATCATTTCA | AAATTACATG | TCAACACTCA | 1740 |
| AATTTTCAAC | AATCGTATTT | TATAAGAATT | CGTTATGCTT | CAAATGGAAG | CGCAAATACA | 1800 |
| CGAGCTGTTA | TAAATCTTAG | TATCCCAGGG | GTAGCAGAAC | TGGGTATGGC | ACTCAACCCC | 1860 |
| ACTTTTTCTG | GTACAGATTA | TACGAATTTA | AAATATAAAG | ATTTTCAGTA | CTTAGAATTT | 1920 |
| TCTAACGAGG | TGAAATTTGC | TCCAAATCAA | AACATATCTC | TTGTGTTTAA | TCGTTCGGAT | 1980 |
| GTATATACAA | ACACAACAGT | ACTTATTGAT | AAAATTGAAT | TTCTGCCAAT | TACTCGTTCT | 2040 |
| ATAAGAGAGG | ATAGAGAGAA | ACAAAAATTA | GAAACAGTAC | AACAAATAAT | TAATACATTT | 2100 |
| TATGCAAATC | CTATAAAAAA | CACTTTACAA | TCAGAACTTA | CAGATTATGA | CATAGATCAA | 2160 |

-continued

```
GCCGCAAATC  TTGTGGAATG  TATTTCTGAA  GAATTATATC  CAAAAGAAAA  AATGCTGTTA   2220
TTAGATGAAG  TTAAAAATGC  GAAACAACTT  AGTCAATCTC  GAAATGTACT  TCAAAACGGG   2280
GATTTTGAAT  CGGCTACGCT  TGGTTGGACA  ACAAGTGATA  ATATCACAAT  TCAAGAAGAT   2340
GATCCTATTT  TTAAAGGGCA  TTACCTTCAT  ATGTCTGGGG  CGAGAGAAAT  TGATGGTACG   2400
ATATTTCCGA  CCTATATATT  CCAAAAAATT  GATGAATCAA  AATTAAAACC  GTATACACGT   2460
TACCTAGTAA  GGGGATTTGT  AGGAAGTAGT  AAAGATGTAG  AACTAGTGGT  TTCACGCTAT   2520
GGGAAGAAA   TTGATGCCAT  CATGAATGTT  CCAGCTGATT  TAAACTATCT  GTATCCTTCT   2580
ACCTTTGATT  GTGAAGGGTC  TAATCGTTGT  GAGACGTCCG  CTGTGCCGGC  TAACATTGGG   2640
AACACTTCTG  ATATGTCGTA  TTCATGCCAA  TATGATACAG  GAAAAAGCA   TGTCGTATGT   2700
CAGGATTCCC  ATCAATTTAG  TTTCACTATT  GATACAGGGG  CATTAGATAC  AAATGAAAAT   2760
ATAGGGGTTT  GGGTCATGTT  TAAAATATCT  TCTCCAGATG  GATACGCATC  ATTAGATAAT   2820
TTAGAAGTAA  TTGAAGAAGG  GCCAATAGAT  GGGGAAGCAC  TGTCACGCGT  GAAACACATG   2880
GAGAAGAAAT  GGAACGATCA  AATGGAAGCA  AACGTTCGG   AAACACAACA  AGCATATGAT   2940
GTAGCGAAAC  AAGCCATTAA  TGCTTTATTC  ACAAATGTAC  AAGATGAGGC  TTTACAGTTT   3000
GATACGACAC  TCGCTCAAAT  TCAGTACGCT  GAGTATTTGG  TACAATCGAT  TCCATATGTG   3060
TACAATGATT  GGTTGTCAGA  TGTTCCAGGT  ATGAATTATG  ATATCTATGT  AGAGTTGGAT   3120
GCACGAGTGG  CACAAGCGCG  TTATTTGTAT  GATACAAGAA  ATATTATTAA  AAATGGTGAT   3180
TTTACACAAG  GGGTAATGGG  GTGGCATGTA  ACTGGAAATG  CAGACGTACA  ACAAATAGAT   3240
GGTGTTTCTG  TATTGGTTCT  ATCTAATTGG  AGTGCTGGCG  TATCTCAAAA  TGTCCATCTC   3300
CAACATAATC  ATGGGTATGT  CTTACGTGTT  ATTGCCAAAA  AGAAGGACC   TGGAAATGGG   3360
TATGTCACGC  TTATGGATTG  TGAGGAGAAT  CAAGAAAAAT  TGACGTTTAC  GTCTTGTGAA   3420
GAAGGATATA  TTACGAAGAC  AGTAGATGTA  TTCCCAGATA  CAGATCGTGT  ACGAATTGAG   3480
ATAGGCGAAA  CCGAAGGTTC  GTTTTATATC  GAAAGCATTG  AATTAATTTG  CATGAACGAG   3540
TGA                                                                     3543
```

( 2 ) INFORMATION FOR SEQ ID NO:28:

( i ) SEQUENCE CHARACTERISTICS:
        ( A ) LENGTH: 1180 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

```
Met  Asn  Pro  Tyr  Gln  Asn  Lys  Asn  Glu  Tyr  Glu  Thr  Leu  Asn  Ala  Ser
 1              5                   10                      15

Gln  Lys  Lys  Leu  Asn  Ile  Ser  Asn  Asn  Tyr  Thr  Arg  Tyr  Pro  Ile  Glu
                20                  25                      30

Asn  Ser  Pro  Lys  Gln  Leu  Leu  Gln  Ser  Thr  Asn  Tyr  Lys  Asp  Trp  Leu
             35                  40                      45

Asn  Met  Cys  Gln  Gln  Asn  Gln  Gln  Tyr  Gly  Gly  Asp  Phe  Glu  Thr  Phe
         50                   55                      60

Ile  Asp  Ser  Gly  Glu  Leu  Ser  Ala  Tyr  Thr  Ile  Val  Val  Gly  Thr  Val
65                       70                      75                      80

Leu  Thr  Gly  Phe  Gly  Phe  Thr  Thr  Pro  Leu  Gly  Leu  Ala  Leu  Ile  Gly
                 85                   90                      95
```

```
Phe Gly Thr Leu Ile Pro Val Leu Phe Pro Ala Gln Asp Gln Ser Asn
            100             105             110

Thr Trp Ser Asp Phe Ile Thr Gln Thr Lys Asn Ile Ile Lys Lys Glu
        115             120             125

Ile Ala Ser Thr Tyr Ile Ser Asn Ala Asn Lys Ile Leu Asn Arg Ser
    130             135             140

Phe Asn Val Ile Ser Thr Tyr His Asn His Leu Lys Thr Trp Glu Asn
145             150             155                         160

Asn Pro Asn Pro Gln Asn Thr Gln Asp Val Arg Thr Gln Ile Gln Leu
                165             170             175

Val His Tyr His Phe Gln Asn Val Ile Pro Glu Leu Val Asn Ser Cys
            180             185             190

Pro Pro Asn Pro Ser Asp Cys Asp Tyr Tyr Asn Ile Leu Val Leu Ser
            195             200             205

Ser Tyr Ala Gln Ala Ala Asn Leu His Leu Thr Val Leu Asn Gln Ala
    210             215             220

Val Lys Phe Glu Ala Tyr Leu Lys Asn Asn Arg Gln Phe Asp Tyr Leu
225             230             235                         240

Glu Pro Leu Pro Thr Ala Ile Asp Tyr Tyr Pro Val Leu Thr Lys Ala
                245             250             255

Ile Glu Asp Tyr Thr Asn Tyr Cys Val Thr Thr Tyr Lys Lys Gly Leu
            260             265             270

Asn Leu Ile Lys Thr Thr Pro Asp Ser Asn Leu Asp Gly Asn Ile Asn
            275             280             285

Trp Asn Thr Tyr Asn Thr Tyr Arg Thr Lys Met Thr Thr Ala Val Leu
    290             295             300

Asp Leu Val Ala Leu Phe Pro Asn Tyr Asp Val Gly Lys Tyr Pro Ile
305             310             315                         320

Gly Val Gln Ser Glu Leu Thr Arg Glu Ile Tyr Gln Val Leu Asn Phe
                325             330             335

Glu Glu Ser Pro Tyr Lys Tyr Tyr Asp Phe Gln Tyr Gln Glu Asp Ser
            340             345             350

Leu Thr Arg Arg Pro His Leu Phe Thr Trp Leu Asp Ser Leu Asn Phe
        355             360             365

Tyr Glu Lys Ala Gln Thr Thr Pro Asn Asn Phe Phe Thr Ser His Tyr
    370             375             380

Asn Met Phe His Tyr Thr Leu Asp Asn Ile Ser Gln Lys Ser Ser Val
385             390             395                         400

Phe Gly Asn His Asn Val Thr Asp Lys Leu Lys Ser Leu Gly Leu Ala
                405             410             415

Thr Asn Ile Tyr Ile Phe Leu Leu Asn Val Ile Ser Leu Asp Asn Lys
            420             425             430

Tyr Leu Asn Asp Tyr Asn Asn Ile Ser Lys Met Asp Phe Phe Ile Thr
        435             440             445

Asn Gly Thr Arg Leu Leu Glu Lys Glu Leu Thr Ala Gly Ser Gly Gln
    450             455             460

Ile Thr Tyr Asp Val Asn Lys Asn Ile Phe Gly Leu Pro Ile Leu Lys
465             470             475                         480

Pro Arg Glu Asn Gln Ala Ile Pro Thr Leu Phe Pro Thr Tyr Asp Asn
                485             490             495

Tyr Ser His Ile Leu Ser Phe Ile Lys Ser Leu Ser Ile Pro Ala Thr
            500             505             510

Tyr Lys Thr Gln Val Tyr Thr Phe Ala Trp Thr His Ser Ser Val Asp
        515             520             525
```

| Pro | Lys | Asn | Thr | Ile | Tyr | Thr | His | Leu | Thr | Thr | Gln | Ile | Pro | Ala | Val |
|---|---|---|---|---|---|---|---|---|---|---|---|---|---|---|---|
| | 530 | | | | 535 | | | | | 540 | | | | | |

| Lys | Ala | Asn | Ser | Leu | Gly | Thr | Ala | Ser | Lys | Val | Val | Gln | Gly | Pro | Gly |
|---|---|---|---|---|---|---|---|---|---|---|---|---|---|---|---|
| 545 | | | | | 550 | | | | 555 | | | | | | 560 |

| His | Thr | Gly | Gly | Asp | Leu | Ile | Asp | Phe | Lys | Asp | His | Phe | Lys | Ile | Thr |
|---|---|---|---|---|---|---|---|---|---|---|---|---|---|---|---|
| | | | | 565 | | | | | 570 | | | | | 575 | |

| Cys | Gln | His | Ser | Asn | Phe | Gln | Gln | Ser | Tyr | Phe | Ile | Arg | Ile | Arg | Tyr |
|---|---|---|---|---|---|---|---|---|---|---|---|---|---|---|---|
| | | | 580 | | | | | 585 | | | | | 590 | | |

| Ala | Ser | Asn | Gly | Ser | Ala | Asn | Thr | Arg | Ala | Val | Ile | Asn | Leu | Ser | Ile |
|---|---|---|---|---|---|---|---|---|---|---|---|---|---|---|---|
| | | 595 | | | | | 600 | | | | | 605 | | | |

| Pro | Gly | Val | Ala | Glu | Leu | Gly | Met | Ala | Leu | Asn | Pro | Thr | Phe | Ser | Gly |
|---|---|---|---|---|---|---|---|---|---|---|---|---|---|---|---|
| | 610 | | | | | 615 | | | | | 620 | | | | |

| Thr | Asp | Tyr | Thr | Asn | Leu | Lys | Tyr | Lys | Asp | Phe | Gln | Tyr | Leu | Glu | Phe |
|---|---|---|---|---|---|---|---|---|---|---|---|---|---|---|---|
| 625 | | | | | 630 | | | | | 635 | | | | | 640 |

| Ser | Asn | Glu | Val | Lys | Phe | Ala | Pro | Asn | Gln | Asn | Ile | Ser | Leu | Val | Phe |
|---|---|---|---|---|---|---|---|---|---|---|---|---|---|---|---|
| | | | | 645 | | | | | 650 | | | | | 655 | |

| Asn | Arg | Ser | Asp | Val | Tyr | Thr | Asn | Thr | Thr | Val | Leu | Ile | Asp | Lys | Ile |
|---|---|---|---|---|---|---|---|---|---|---|---|---|---|---|---|
| | | | 660 | | | | | 665 | | | | | 670 | | |

| Glu | Phe | Leu | Pro | Ile | Thr | Arg | Ser | Ile | Arg | Glu | Asp | Arg | Glu | Lys | Gln |
|---|---|---|---|---|---|---|---|---|---|---|---|---|---|---|---|
| | | 675 | | | | | 680 | | | | | 685 | | | |

| Lys | Leu | Glu | Thr | Val | Gln | Gln | Ile | Ile | Asn | Thr | Phe | Tyr | Ala | Asn | Pro |
|---|---|---|---|---|---|---|---|---|---|---|---|---|---|---|---|
| | 690 | | | | | 695 | | | | | 700 | | | | |

| Ile | Lys | Asn | Thr | Leu | Gln | Ser | Glu | Leu | Thr | Asp | Tyr | Asp | Ile | Asp | Gln |
|---|---|---|---|---|---|---|---|---|---|---|---|---|---|---|---|
| 705 | | | | | 710 | | | | | 715 | | | | | 720 |

| Ala | Ala | Asn | Leu | Val | Glu | Cys | Ile | Ser | Glu | Glu | Leu | Tyr | Pro | Lys | Glu |
|---|---|---|---|---|---|---|---|---|---|---|---|---|---|---|---|
| | | | | 725 | | | | | 730 | | | | | 735 | |

| Lys | Met | Leu | Leu | Leu | Asp | Glu | Val | Lys | Asn | Ala | Lys | Gln | Leu | Ser | Gln |
|---|---|---|---|---|---|---|---|---|---|---|---|---|---|---|---|
| | | | 740 | | | | | 745 | | | | | 750 | | |

| Ser | Arg | Asn | Val | Leu | Gln | Asn | Gly | Asp | Phe | Glu | Ser | Ala | Thr | Leu | Gly |
|---|---|---|---|---|---|---|---|---|---|---|---|---|---|---|---|
| | | 755 | | | | | 760 | | | | | 765 | | | |

| Trp | Thr | Thr | Ser | Asp | Asn | Ile | Thr | Ile | Gln | Glu | Asp | Asp | Pro | Ile | Phe |
|---|---|---|---|---|---|---|---|---|---|---|---|---|---|---|---|
| | 770 | | | | | 775 | | | | | 780 | | | | |

| Lys | Gly | His | Tyr | Leu | His | Met | Ser | Gly | Ala | Arg | Glu | Ile | Asp | Gly | Thr |
|---|---|---|---|---|---|---|---|---|---|---|---|---|---|---|---|
| 785 | | | | | 790 | | | | | 795 | | | | | 800 |

| Ile | Phe | Pro | Thr | Tyr | Ile | Phe | Gln | Lys | Ile | Asp | Glu | Ser | Lys | Leu | Lys |
|---|---|---|---|---|---|---|---|---|---|---|---|---|---|---|---|
| | | | | 805 | | | | | 810 | | | | | 815 | |

| Pro | Tyr | Thr | Arg | Tyr | Leu | Val | Arg | Gly | Phe | Val | Gly | Ser | Ser | Lys | Asp |
|---|---|---|---|---|---|---|---|---|---|---|---|---|---|---|---|
| | | | 820 | | | | | 825 | | | | | 830 | | |

| Val | Glu | Leu | Val | Val | Ser | Arg | Tyr | Gly | Glu | Glu | Ile | Asp | Ala | Ile | Met |
|---|---|---|---|---|---|---|---|---|---|---|---|---|---|---|---|
| | | 835 | | | | | 840 | | | | | 845 | | | |

| Asn | Val | Pro | Ala | Asp | Leu | Asn | Tyr | Leu | Tyr | Pro | Ser | Thr | Phe | Asp | Cys |
|---|---|---|---|---|---|---|---|---|---|---|---|---|---|---|---|
| 850 | | | | | 855 | | | | | 860 | | | | | |

| Glu | Gly | Ser | Asn | Arg | Cys | Glu | Thr | Ser | Ala | Val | Pro | Ala | Asn | Ile | Gly |
|---|---|---|---|---|---|---|---|---|---|---|---|---|---|---|---|
| 865 | | | | | 870 | | | | | 875 | | | | | 880 |

| Asn | Thr | Ser | Asp | Met | Ser | Tyr | Ser | Cys | Gln | Tyr | Asp | Thr | Gly | Lys | Lys |
|---|---|---|---|---|---|---|---|---|---|---|---|---|---|---|---|
| | | | | 885 | | | | | 890 | | | | | 895 | |

| His | Val | Val | Cys | Gln | Asp | Ser | His | Gln | Phe | Ser | Phe | Thr | Ile | Asp | Thr |
|---|---|---|---|---|---|---|---|---|---|---|---|---|---|---|---|
| | | | 900 | | | | | 905 | | | | | 910 | | |

| Gly | Ala | Leu | Asp | Thr | Asn | Glu | Asn | Ile | Gly | Val | Trp | Val | Met | Phe | Lys |
|---|---|---|---|---|---|---|---|---|---|---|---|---|---|---|---|
| | | 915 | | | | | 920 | | | | | 925 | | | |

| Ile | Ser | Ser | Pro | Asp | Gly | Tyr | Ala | Ser | Leu | Asp | Asn | Leu | Glu | Val | Ile |
|---|---|---|---|---|---|---|---|---|---|---|---|---|---|---|---|
| | 930 | | | | | 935 | | | | | 940 | | | | |

| Glu | Glu | Gly | Pro | Ile | Asp | Gly | Glu | Ala | Leu | Ser | Arg | Val | Lys | His | Met |
|---|---|---|---|---|---|---|---|---|---|---|---|---|---|---|---|

|     |     |     |     | 945 |     |     |     | 950 |     |     |     | 955 |     |     |     | 960 |
| --- | --- | --- | --- | --- | --- | --- | --- | --- | --- | --- | --- | --- | --- | --- | --- | --- |
| Glu | Lys | Lys | Trp | Asn | Asp | Gln | Met | Glu | Ala | Lys | Arg | Ser | Glu | Thr | Gln |
|     |     |     |     |     | 965 |     |     |     |     | 970 |     |     |     |     | 975 |
| Gln | Ala | Tyr | Asp | Val | Ala | Lys | Gln | Ala | Ile | Asn | Ala | Leu | Phe | Thr | Asn |
|     |     |     |     | 980 |     |     |     |     | 985 |     |     |     |     | 990 |     |
| Val | Gln | Asp | Glu | Ala | Leu | Gln | Phe | Asp | Thr | Thr | Leu | Ala | Gln | Ile | Gln |
|     |     |     | 995 |     |     |     |     | 1000 |     |     |     |     | 1005 |     |     |
| Tyr | Ala | Glu | Tyr | Leu | Val | Gln | Ser | Ile | Pro | Tyr | Val | Tyr | Asn | Asp | Trp |
|     | 1010 |     |     |     |     | 1015 |     |     |     |     | 1020 |     |     |     |     |
| Leu | Ser | Asp | Val | Pro | Gly | Met | Asn | Tyr | Asp | Ile | Tyr | Val | Glu | Leu | Asp |
| 1025 |     |     |     |     | 1030 |     |     |     |     | 1035 |     |     |     |     | 1040 |
| Ala | Arg | Val | Ala | Gln | Ala | Arg | Tyr | Leu | Tyr | Asp | Thr | Arg | Asn | Ile | Ile |
|     |     |     |     | 1045 |     |     |     |     | 1050 |     |     |     |     | 1055 |     |
| Lys | Asn | Gly | Asp | Phe | Thr | Gln | Gly | Val | Met | Gly | Trp | His | Val | Thr | Gly |
|     |     |     | 1060 |     |     |     |     | 1065 |     |     |     |     | 1070 |     |     |
| Asn | Ala | Asp | Val | Gln | Gln | Ile | Asp | Gly | Val | Ser | Val | Leu | Val | Leu | Ser |
|     |     | 1075 |     |     |     |     | 1080 |     |     |     |     | 1085 |     |     |     |
| Asn | Trp | Ser | Ala | Gly | Val | Ser | Gln | Asn | Val | His | Leu | Gln | His | Asn | His |
|     | 1090 |     |     |     |     | 1095 |     |     |     |     | 1100 |     |     |     |     |
| Gly | Tyr | Val | Leu | Arg | Val | Ile | Ala | Lys | Lys | Glu | Gly | Pro | Gly | Asn | Gly |
| 1105 |     |     |     |     | 1110 |     |     |     |     | 1115 |     |     |     |     | 1120 |
| Tyr | Val | Thr | Leu | Met | Asp | Cys | Glu | Glu | Asn | Gln | Glu | Lys | Leu | Thr | Phe |
|     |     |     |     | 1125 |     |     |     |     | 1130 |     |     |     |     | 1135 |     |
| Thr | Ser | Cys | Glu | Glu | Gly | Tyr | Ile | Thr | Lys | Thr | Val | Asp | Val | Phe | Pro |
|     |     |     | 1140 |     |     |     |     | 1145 |     |     |     |     | 1150 |     |     |
| Asp | Thr | Asp | Arg | Val | Arg | Ile | Glu | Ile | Gly | Glu | Thr | Glu | Gly | Ser | Phe |
|     |     | 1155 |     |     |     |     | 1160 |     |     |     |     | 1165 |     |     |     |
| Tyr | Ile | Glu | Ser | Ile | Glu | Leu | Ile | Cys | Met | Asn | Glu |     |     |     |     |
|     | 1170 |     |     |     |     | 1175 |     |     |     | 1180 |     |     |     |     |     |

( 2 ) INFORMATION FOR SEQ ID NO:29:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:29:

| CCAAGGGCGT | TTTTACACAA | GAAATTCTCG | AGAC |  | 3 4 |
| --- | --- | --- | --- | --- | --- |

( 2 ) INFORMATION FOR SEQ ID NO:30:

( i ) SEQUENCE CHARACTERISTICS:
        ( A ) LENGTH: 2061 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

| ATGAATCCAT | ATCAAAATAA | GAATGAATAT | GAAATATTCA | ATGCTCCATC | CAATGGTTTT | 6 0 |
| --- | --- | --- | --- | --- | --- | --- |
| AGCAAGTCTA | ATAACTATTC | TAGATATCCA | TTAGCAAATA | AGCCAAATCA | ACCACTGAAA | 1 2 0 |
| AACACGAATT | ACAAAGATTG | GCTCAATGTG | TGTCAAGATA | ATCAACAATA | TGGCAATAAT | 1 8 0 |
| GCGGGGAATT | TTGTTAGTTC | TGAAACTATT | GTTGGAGTTA | GTGCAGGTAT | TATTGTAGTA | 2 4 0 |

-continued

| | | | | | |
|---|---|---|---|---|---|
| GGAACTATGT | TAGGAGCTTT | TGCTGCCCCT | GTCTTAGCTG | CAGGTATAAT | ATCTTTTGGG 300 |
| ACTTTGTTGC | CGATCTTTTG | GCAAGGATCT | GACCCTGCAA | ATGTTTGGCA | GGATTTGTTA 360 |
| AACATCGGAG | GAAGGCCTAT | ACAAGAAATA | GATAAAACA | TAATTAATGT | ACTAACTTCT 420 |
| ATCGTAACAC | CTATAAAAAA | TCAACTTGAT | AAATATCAAG | AATTTTTCGA | TAAATGGGAG 480 |
| CCAGCACGTA | CACACGCTAA | TGCTAAAGCA | GTACATGATC | TCTTACTAC | CTTAGAACCT 540 |
| ATAATAGATA | AAGATTTAGA | TATGTTAAAA | AATAATGCTA | GCTATCGAAT | ACCAACACTC 600 |
| CCTGCATATG | CACAAATAGC | TACTTGGCAC | TTGAATTTAT | TAAAACATGC | TGCTACCTAT 660 |
| TACAATATAT | GGCTGCAAAA | TCAAGGTATA | AATCCAAGTA | CTTTCAATTC | ATCTAATTAC 720 |
| TATCAGGGCT | ATTTAAAACG | TAAAATACAA | GAATATACTG | ACTATTGTAT | ACAAACGTAC 780 |
| AATGCAGGAC | TAACTATGAT | TAGAACTAAT | ACTAACGCAA | CATGGAATAT | GTATAATACT 840 |
| TACCGTTTAG | AAATGACTCT | AACTGTGTTA | GATCTTATTG | CTATTTTTCC | AAATTATGAC 900 |
| CCAGAAAAAT | ATCCAATAGG | AGTTAAATCT | GAACTTACCA | GAGAAGTTTA | TACGAATGTT 960 |
| AATTCAGATA | CATTTAGAAC | CATAACAGAA | CTAGAAAATG | GATTAACTAG | AAATCCTACA 1020 |
| TTATTTACTT | GGATAAACCA | AGGGCGTTTT | TACACAAGAA | ATTCTCGAGA | CATTCTTGAT 1080 |
| CCTTATGATA | TTTTTTCTTT | TACAGGTAAC | CAGATGGCCT | TTACACATAC | TAATGATGAT 1140 |
| CGCAACATAA | TCTGGGGAGC | GGTTCATGGA | CATATTATTT | CTCAAGACAC | ATCCAAAGTA 1200 |
| TTTCCTTTTT | ATAGAAACAA | ACCTATTGAT | AAGGTCGAAA | TTGTCAGACA | TAGAGAGTAC 1260 |
| TCAGATATAA | TATATGAAAT | GATATTTTTT | TCGAATAGCA | GTGAAGTATT | TCGATATTCA 1320 |
| TCCAATTCAA | CAATAGAAAA | TAATTATAAA | AGAACTGATT | CTTATATGAT | TCCAAAACAA 1380 |
| ACATGGAAAA | ATAAAGAATA | TGGTCATACT | CTATCGTATA | TAAAAACTGA | TAATTATATA 1440 |
| TTTTCAGTAG | TTAGAGAAAG | AAGAAGAGTT | GCATTTAGTT | GGACACATAC | TAGTGTTGAT 1500 |
| TTCCAAAATA | CAATAGATTT | AGATAACATC | ACCCAAATCC | ACGCTCTAAA | AGCTTTGAAG 1560 |
| GTAAGTTCTG | ATTCGAAAAT | TGTGAAAGGT | CCTGGTCACA | CAGGTGGAGA | CTTGGTAATT 1620 |
| CTTAAAGATA | GTATGGATTT | TAGAGTTAGA | TTTTTAAAAA | ATGTTTCTCG | ACAATATCAA 1680 |
| GTACGTATTC | GTTATGCTAC | TAATGCTCCA | AAGACAACAG | TATTCTTAAC | CGGAATAGAT 1740 |
| ACTATAAGTG | TGGAGCTCCC | TAGTACCACT | TCCCGCCAAA | ACCCAAATGC | TACAGATTTA 1800 |
| ACATATGCAG | ATTTTGGATA | TGTAACATTT | CCAAGAACAG | TTCCAAATAA | AACATTTGAA 1860 |
| GGAGAAGACA | CTTTATTAAT | GACCTTATAT | GGTACACCAA | ATCATTCATA | TAATATATAT 1920 |
| ATTGACAAAA | TCGAATTTAT | TCCAATCACT | CAATCTGTAT | TAGATTATAC | AGAGAAGCAA 1980 |
| AATATAGAAA | AAACACAGAA | AATAGTGAAT | GATTTATTTG | TTAATTAAAA | CAAAGTTCTT 2040 |
| ACTAAAATAG | ATAGTATGGC | T | | | 2061 |

( 2 ) INFORMATION FOR SEQ ID NO:31:

( i ) SEQUENCE CHARACTERISTICS:
        ( A ) LENGTH: 686 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:31:

Met Asn Pro Tyr Gln Asn Lys Asn Glu Tyr Glu Ile Phe Asn Ala Pro
    1               5                   10                  15

Ser Asn Gly Phe Ser Lys Ser Asn Asn Tyr Ser Arg Tyr Pro Leu Ala
                20                  25                  30

-continued

```
Asn  Lys  Pro  Asn  Gln  Pro  Leu  Lys  Asn  Thr  Asn  Tyr  Lys  Asp  Trp  Leu
          35                       40                      45

Asn  Val  Cys  Gln  Asp  Asn  Gln  Gln  Tyr  Gly  Asn  Asn  Ala  Gly  Asn  Phe
     50                       55                  60

Val  Ser  Ser  Glu  Thr  Ile  Val  Gly  Val  Ser  Ala  Gly  Ile  Ile  Val  Val
65                            70                  75                           80

Gly  Thr  Met  Leu  Gly  Ala  Phe  Ala  Ala  Pro  Val  Leu  Ala  Ala  Gly  Ile
                    85                       90                           95

Ile  Ser  Phe  Gly  Thr  Leu  Leu  Pro  Ile  Phe  Trp  Gln  Gly  Ser  Asp  Pro
               100                      105                 110

Ala  Asn  Val  Trp  Gln  Asp  Leu  Leu  Asn  Ile  Gly  Gly  Arg  Pro  Ile  Gln
          115                      120                      125

Glu  Ile  Asp  Lys  Asn  Ile  Ile  Asn  Val  Leu  Thr  Ser  Ile  Val  Thr  Pro
     130                      135                 140

Ile  Lys  Asn  Gln  Leu  Asp  Lys  Tyr  Gln  Glu  Phe  Phe  Asp  Lys  Trp  Glu
145                      150                      155                      160

Pro  Ala  Arg  Thr  His  Ala  Asn  Ala  Lys  Ala  Val  His  Asp  Leu  Phe  Thr
                    165                 170                      175

Thr  Leu  Glu  Pro  Ile  Ile  Asp  Lys  Asp  Leu  Asp  Met  Leu  Lys  Asn  Asn
               180                 185                           190

Ala  Ser  Tyr  Arg  Ile  Pro  Thr  Leu  Pro  Ala  Tyr  Ala  Gln  Ile  Ala  Thr
          195                      200                      205

Trp  His  Leu  Asn  Leu  Leu  Lys  His  Ala  Ala  Thr  Tyr  Tyr  Asn  Ile  Trp
     210                      215                 220

Leu  Gln  Asn  Gln  Gly  Ile  Asn  Pro  Ser  Thr  Phe  Asn  Ser  Ser  Asn  Tyr
225                      230                      235                      240

Tyr  Gln  Gly  Tyr  Leu  Lys  Arg  Lys  Ile  Gln  Glu  Tyr  Thr  Asp  Tyr  Cys
                    245                      250                      255

Ile  Gln  Thr  Tyr  Asn  Ala  Gly  Leu  Thr  Met  Ile  Arg  Thr  Asn  Thr  Asn
               260                      265                 270

Ala  Thr  Trp  Asn  Met  Tyr  Asn  Thr  Tyr  Arg  Leu  Glu  Met  Thr  Leu  Thr
          275                      280                      285

Val  Leu  Asp  Leu  Ile  Ala  Ile  Phe  Pro  Asn  Tyr  Asp  Pro  Glu  Lys  Tyr
290                      295                      300

Pro  Ile  Gly  Val  Lys  Ser  Glu  Leu  Thr  Arg  Glu  Val  Tyr  Thr  Asn  Val
305                 310                      315                           320

Asn  Ser  Asp  Thr  Phe  Arg  Thr  Ile  Thr  Glu  Leu  Glu  Asn  Gly  Leu  Thr
                    325                 330                      335

Arg  Asn  Pro  Thr  Leu  Phe  Thr  Trp  Ile  Asn  Gln  Gly  Arg  Phe  Tyr  Thr
               340                 345                      350

Arg  Asn  Ser  Arg  Asp  Ile  Leu  Asp  Pro  Tyr  Asp  Ile  Phe  Ser  Phe  Thr
          355                      360                 365

Gly  Asn  Gln  Met  Ala  Phe  Thr  His  Thr  Asn  Asp  Asp  Arg  Asn  Ile  Ile
     370                      375                      380

Trp  Gly  Ala  Val  His  Gly  His  Ile  Ile  Ser  Gln  Asp  Thr  Ser  Lys  Val
385                      390                      395                      400

Phe  Pro  Phe  Tyr  Arg  Asn  Lys  Pro  Ile  Asp  Lys  Val  Glu  Ile  Val  Arg
                    405                      410                      415

His  Arg  Glu  Tyr  Ser  Asp  Ile  Ile  Tyr  Glu  Met  Ile  Phe  Phe  Ser  Asn
               420                      425                 430

Ser  Ser  Glu  Val  Phe  Arg  Tyr  Ser  Ser  Asn  Ser  Thr  Ile  Glu  Asn  Asn
          435                      440                      445

Tyr  Lys  Arg  Thr  Asp  Ser  Tyr  Met  Ile  Pro  Lys  Gln  Thr  Trp  Lys  Asn
```

-continued

|   | | | | 450 | | | | | 455 | | | | | 460 | |
|---|---|---|---|---|---|---|---|---|---|---|---|---|---|---|---|
| Lys 465 | Glu | Tyr | Gly | His | Thr 470 | Leu | Ser | Tyr | Ile | Lys 475 | Thr | Asp | Asn | Tyr | Ile 480 |
| Phe | Ser | Val | Val | Arg 485 | Glu | Arg | Arg | Arg | Val 490 | Ala | Phe | Ser | Trp | Thr 495 | His |
| Thr | Ser | Val | Asp 500 | Phe | Gln | Asn | Thr | Ile 505 | Asp | Leu | Asp | Asn | Ile 510 | Thr | Gln |
| Ile | His | Ala 515 | Leu | Lys | Ala | Leu | Lys 520 | Val | Ser | Ser | Asp | Ser 525 | Lys | Ile | Val |
| Lys | Gly 530 | Pro | Gly | His | Thr | Gly 535 | Gly | Asp | Leu | Val | Ile 540 | Leu | Lys | Asp | Ser |
| Met 545 | Asp | Phe | Arg | Val | Arg 550 | Phe | Leu | Lys | Asn | Val 555 | Ser | Arg | Gln | Tyr | Gln 560 |
| Val | Arg | Ile | Arg | Tyr 565 | Ala | Thr | Asn | Ala | Pro 570 | Lys | Thr | Thr | Val | Phe 575 | Leu |
| Thr | Gly | Ile | Asp 580 | Thr | Ile | Ser | Val | Glu 585 | Leu | Pro | Ser | Thr | Thr 590 | Ser | Arg |
| Gln | Asn | Pro 595 | Asn | Ala | Thr | Asp | Leu 600 | Thr | Tyr | Ala | Asp | Phe 605 | Gly | Tyr | Val |
| Thr | Phe 610 | Pro | Arg | Thr | Val | Pro 615 | Asn | Lys | Thr | Phe | Glu 620 | Gly | Glu | Asp | Thr |
| Leu 625 | Leu | Met | Thr | Leu | Tyr 630 | Gly | Thr | Pro | Asn | His 635 | Ser | Tyr | Asn | Ile | Tyr 640 |
| Ile | Asp | Lys | Ile | Glu 645 | Phe | Ile | Pro | Ile | Thr 650 | Gln | Ser | Val | Leu | Asp 655 | Tyr |
| Thr | Glu | Lys | Gln 660 | Asn | Ile | Glu | Lys | Thr 665 | Gln | Lys | Ile | Val | Asn 670 | Asp | Leu |
| Phe | Val | Asn 675 | Asn | Lys | Val | Leu | Thr 680 | Lys | Ile | Asp | Ser | Met 685 | Ala | | |